(12) United States Patent
Kurochi

(10) Patent No.: US 8,451,977 B2
(45) Date of Patent: May 28, 2013

(54) COLLIMATOR MODULE, X-RAY DETECTOR, X-RAY CT DEVICE, AND ASSEMBLING METHOD OF COLLIMATOR MODULE

(75) Inventor: Haruo Kurochi, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 273 days.

(21) Appl. No.: 12/910,651

(22) Filed: Oct. 22, 2010

(65) Prior Publication Data

US 2011/0096895 A1 Apr. 28, 2011

(30) Foreign Application Priority Data

Oct. 23, 2009 (JP) .................................. 2009-244585

(51) Int. Cl.
*G21K 1/02* (2006.01)

(52) U.S. Cl.
USPC ............................................ 378/147; 378/19

(58) Field of Classification Search
USPC ................ 378/19, 147, 149, 154; 250/370.09
See application file for complete search history.

(56) References Cited

U.S. PATENT DOCUMENTS

| 6,587,538 | B2 | 7/2003 | Igarashi et al. |
| 2009/0225955 | A1* | 9/2009 | Igarashi et al. ............... 378/149 |

FOREIGN PATENT DOCUMENTS

JP 2007117677 5/2007

OTHER PUBLICATIONS

Japanese Office Action; Application No. 2009-244585; dated Aug. 9, 2011; p. 2.

* cited by examiner

*Primary Examiner* — Jurie Yun
(74) *Attorney, Agent, or Firm* — Armstrong Teasdale LLP

(57) ABSTRACT

A collimator module (10A) comprises a plurality of collimator single plates (11) having a pair of long sides and a pair of short sides and a pair of blocks (12) including a plurality of first grooves (125) extending along an irradiation direction of the X-rays. The short sides are inserted into the first grooves to support the collimator single plates. A supporting member is configured to cover the long sides from an incident side and an emission side of the X-rays. The supporting member includes an incident side fixing sheet (13) and an emission side fixing sheet (15) each having a plurality of second grooves into which the long sides are inserted to support the plurality of collimator single plates. The fixing sheets cover the first grooves and at least a portion of each of the long sides.

20 Claims, 18 Drawing Sheets

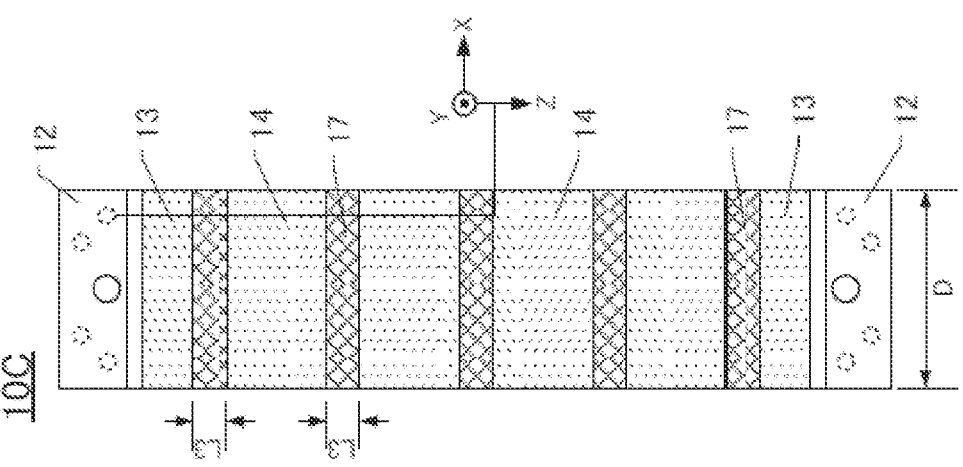

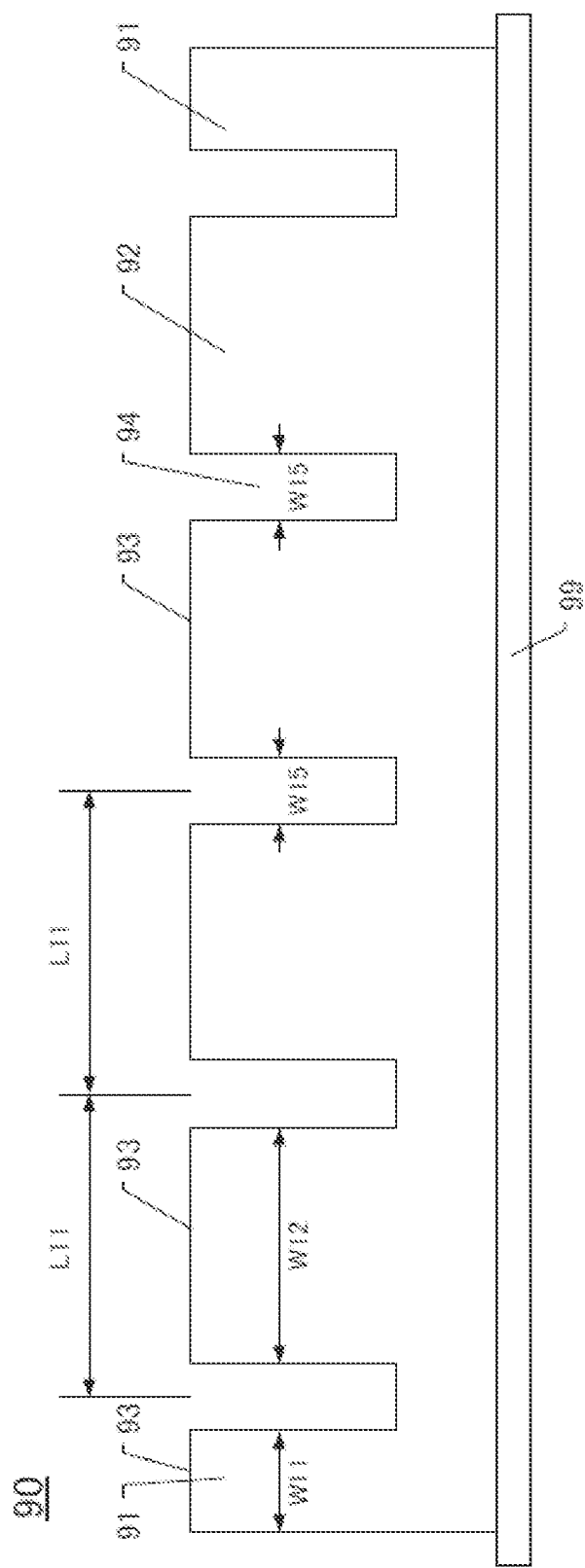

COLLIMATOR MODULE, X-RAY DETECTOR, X-RAY CT DEVICE, AND ASSEMBLING METHOD OF COLLIMATOR MODULE

CROSS REFERENCE TO RELATED APPLICATIONS

This application claims the benefit of Japanese Patent Application No. 2009-244585 filed Oct. 23, 2009, which is hereby incorporated by reference in its entirety.

BACKGROUND OF THE INVENTION

This invention relates to collimator modules for removing scattered X-rays in X-ray detectors and an assembling method thereof. Also, this invention relates to X-ray detectors and X-ray CT (Computed Tomography) devices.

X-ray CT devices arrange a detector unit comprising a scintillator for detecting X-rays with respect to an X-ray tube. This detector unit includes a plurality of detector units arrayed in a circular-arc fashion. In the detector unit, an X-ray collimator is arranged between the scintillator and a subject such that only X-rays passed through the subject, not X-rays reflected by the subject, reaches the scintillator.

The X-ray CT device disclosed in U.S. Pat. No. 6,587,538 has a base member arranged along a channel direction, a plurality of collimator modules arranged along the channel direction, and a detector unit corresponding to the plurality of collimator modules. The collimator module holds only long sides of a collimator single plate that has a rectangle shape extending in a slice direction by a support member.

SUMMARY OF THE INVENTION

The collimator module disclosed in U.S. Pat. No. 6,587,538 only holds the long sides of the collimator single plates so that the short sides of the collimator module are not held strongly. With desired improvement of the quality of X-ray CT devices, the holding positions of the collimator single plate must be accurate, but the supporting member disclosed in U.S. Pat. No. 6,587,538 only inserts the long sides of the collimator single plate into grooves.

Recently, X-ray detectors used for X-ray CT devices are grown to be multi-detectors having detector-rows of 16 or 64, but the device having detector-rows of 128 or 320 has been proposed. If collimator modules are used for such multi-detector CT having more than 100 detector-rows, the length of the collimator modules in a slice direction (a row direction of the X-ray detector) becomes longer. Thus, if the X-ray detector having collimator modules rotates at a high speed, the collimator single plates are easily bent. Therefore, if the collimator modules disclosed in U.S. Pat. No. 6,587,538 are used, the collimator modules cannot resist the high-speed rotation.

The present invention solves the above-mentioned problem by providing collimator modules, X-ray detectors, and a X-ray CT device that are not easily bent at the high-speed rotation of the X-ray detector having the collimator module, and also by providing assembling methods of such collimator modules.

A collimator module of a first aspect comprises a plurality of collimator single plates including a rectangle shape having a pair of long sides and a pair of short sides shorter than of the pair of long sides, a pair of blocks including a plurality of first grooves extending along an irradiation direction of the X-rays to which the short sides are inserted and supporting the plurality of collimator single plates which are inserted to the grooves so as to be vertically installed along the irradiation direction of X-rays, and a supporting member configured to cover the long side of the plurality of the collimator single plates from an incident side and an emission side of the X-rays and having X-ray transmission property, wherein the supporting member comprising an incident side fixing sheet and an emission side fixing sheet each having a plurality of second grooves to which the long sides of the collimator single plates are inserted and supporting the plurality of collimator single plates by covering from the incident side and the emission side of the X-rays the plurality of first grooves of the pair of blocks and at least a portion of each of the long sides of the plurality of collimator single plates adjacent to the first grooves with the short sides inserted to the first grooves and the long sides inserted to the second grooves.

An X-ray detector of a second aspect comprises a plurality of collimator single plates including a rectangle shape having a pair of long sides and a pair of short sides shorter than of the pair of long sides, a pair of blocks including a plurality of first grooves extending along an irradiation direction of the X-rays to which the short sides are inserted and supporting the plurality of collimator single plates which are inserted to the grooves so as to be vertically installed along the irradiation direction of X-rays, a supporting member configured to cover the long side of the plurality of the collimator single plates from an incident side and an emission side of the X-rays and having X-ray transmission property, wherein the supporting member comprising an incident side fixing sheet and an emission side fixing sheet each having a plurality of second grooves to which the long sides of the collimator single plates are inserted and supporting the plurality of collimator single plates by covering from the incident side and the emission side of the X-rays the plurality of first grooves of the pair of blocks and at least a portion of each of the long sides of the plurality of collimator single plates adjacent to the first grooves with the short sides inserted to the first grooves and the long sides inserted to the second grooves, a detection element configured to detect X-rays which pass through spaces defined between the collimator single plates and fixed to the pair of blocks, and a base member having a plurality of positioning portions placed along an circular-arc fashion for fixing the pair of blocks to a reference position.

An X-ray CT device of a third aspect comprises a plurality of collimator single plates including a rectangle shape having a pair of long sides and a pair of short sides shorter than of the pair of long sides, a pair of blocks including a plurality of first grooves extending along an irradiation direction of the X-rays to which the short sides are inserted and supporting the plurality of collimator single plates which are inserted to the grooves so as to be vertically installed along the irradiation direction of X-rays, and a supporting member configured to cover the long side of the plurality of the collimator single plates from an incident side and an emission side of the X-rays and having X-ray transmission property, wherein the supporting member comprising an incident side fixing sheet and an emission side fixing sheet each having a plurality of second grooves to which the long sides of the collimator single plates are inserted and supporting the plurality of collimator single plates by covering from the incident side and the emission side of the X-rays the plurality of first grooves of the pair of blocks and at least a portion of each of the long sides of the plurality of collimator single plates adjacent to the first grooves with the short sides inserted to the first grooves and the long sides inserted to the second grooves, a detection element configured to detect X-rays which pass through spaces defined between the collimator single plates and fixed to the pair of blocks, and a base member having a plurality of positioning portions placed along an circular-arc fashion for fixing the pair of blocks to a reference position.

A method for assembling of a collimator module which has a plurality of collimator single plates including a rectangle shape having a pair of long sides and a pair of short sides shorter than of the pair of long sides, a pair of blocks including a plurality of first grooves extending along an irradiation direction of the X-rays to which the short sides are inserted and supporting the plurality of collimator single plates which are inserted to the grooves so as to be vertically installed along the irradiation direction of X-rays, and a supporting member configured to cover the long side of the plurality of the collimator single plates from an incident side and an emission side of the X-rays and having X-ray transmission property, wherein the supporting member comprising a first incident side fixing sheet and a first emission side fixing sheet each having a plurality of second grooves to which the long sides of the collimator single plates are inserted and supporting the plurality of collimator single plates by covering from the incident side and the emission side of the X-rays the plurality of first grooves of the pair of blocks and at least a portion of each of the long sides of the plurality of collimator single plates adjacent to the first grooves with the short sides inserted to the first grooves and the long sides inserted to the second grooves, and a second incident side fixing sheet and a second emission side fixing sheet each having a plurality of second grooves to which the long sides of the collimator single plates are inserted and covering the long sides of the collimator single plates with gaps between those and the first incident side fixing sheet and the first emission side fixing sheet respectively with the long sides of the collimator single plates inserted to the second grooves, the method comprising steps of inserting the short sides of the collimator single plates to the plurality of first grooves of the pair of blocks, arraying the collimator single plates by pushing the collimator single plates to one wall surface of the first groove by a pressing component placed so as to sandwich the long sides of each of the plurality of collimator single plates, fixing the long sides of the collimator single plates to the first incident side fixing sheet and the first emission side fixing sheet, and the second incident side fixing sheet and the second emission side fixing sheet, by placing the first incident side fixing sheet and the first emission side fixing sheet such that the long sides on the incident side and the emission side of the arrayed collimator single plates being inserted to the first grooves of the first incident side fixing sheet and the first emission side fixing sheet, and the second grooves of the second incident side fixing sheet and the second emission side fixing sheet and that the pressing component are arranged to a gap between the first incident side fixing sheet and the first emission side fixing sheet, and between the second incident side fixing sheet and the second emission side fixing sheet, and removing the pressing component from the collimator single plates.

A plurality of first grooves of a pair of blocks and a portion of each of the long sides of a plurality of collimator single plates adjacent to the plurality of first grooves of the pair of blocks are covered from an incident side and an emission side of X-rays where short sides of the collimator single plates are inserted to the first grooves and long sides of the collimator single plates are inserted to the second grooves. Therefore, the strength of the collimator module of present invention is increased and the collimator single plates are not easily bent.

BRIEF DESCRIPTION OF THE DRAWINGS

FIG. 9A is a flat view of the third collimator module 10C.
FIG. 9B is a side view of the third collimator module 10C.
FIG. 15 is a supporting block 90 supporting the first and the second incident side fixing sheet.

DETAILED DESCRIPTION OF THE INVENTION

Overview of X-Ray CT Device 100

Figure 1:
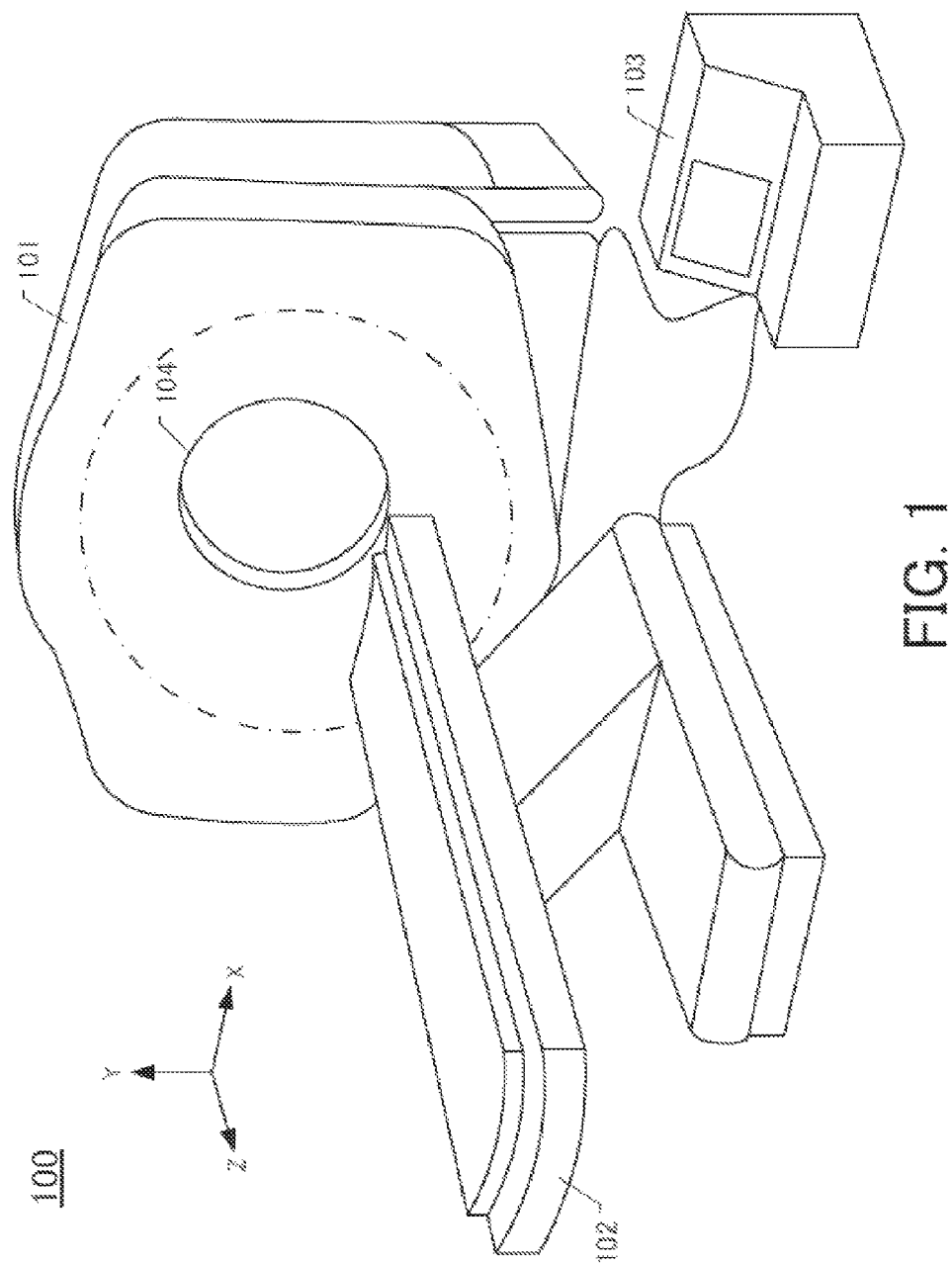
FIG. 1 is a perspective view of a X-ray CT device 100.

FIG. 1 is a perspective view of an X-ray CT (computer tomography) device 100. As shown in FIG. 1, the X-ray CT device has a scanning gantry 101 for scanning a subject S (shown in FIG. 2) and acquiring a projection data and a cradle 102 on which the subject is placed going in to and out of a bore 104 of the scanning gantry 101 which is a scanning area. The X-ray CT device 100 further has an operating console 103 to operate the X-ray CT device 100 and to reconstruct images based on the acquired projection data.

In FIG. 1, a body axis direction of the subject S on the cradle 102 is a Z-axis direction, a direction perpendicular to the ground (to the Z-axis) is Y-axis direction, and a direction orthogonal to the Z-axis and Y-axis is X-direction.

The cradle 102 contains a motor to elevate and to move the cradle 102 horizontally. The subject S is placed on the cradle 102 and the cradle 102 goes in to and out of the bore 104 of the scanning gantry 101.

The operating console 103 is provided with an input device receiving inputs from an operator and a monitor for displaying images. Also, the operating console 103 has a central processing device for controlling each member to acquire the projection data of the subject or processing three-dimensional image reconstruction, a data acquisition buffer for acquiring obtained data by the scanning gantry 101, and a memory device for memorizing programs, data, and the like.

Figure 2:
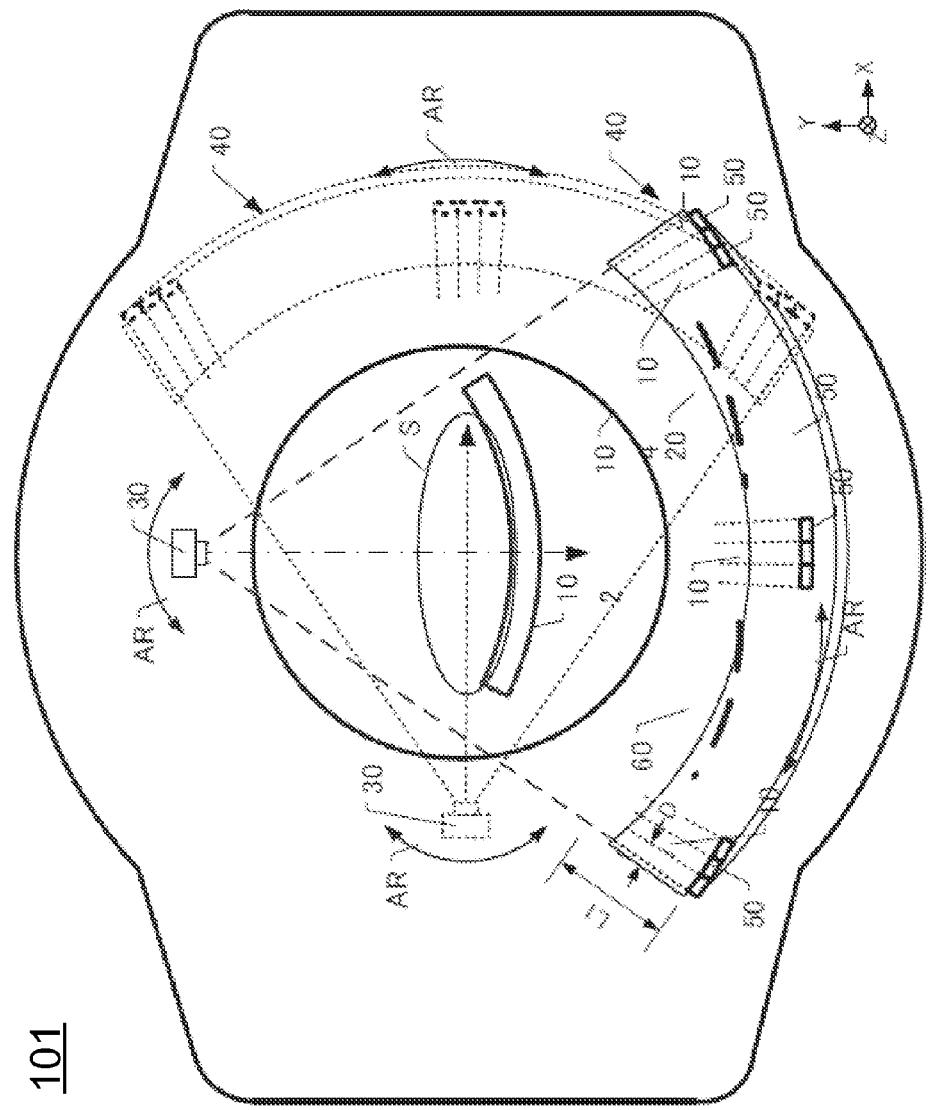
FIG. 2 is a schematic view for explaining the scanning gantry 101.

FIG. 2 is a schematic view for explaining the scanning gantry 101. As shown in FIG. 2, the scanning gantry 101 has an X-ray tube 30 for scanning the subject S and an X-ray detector 40. In the X-ray CT device 100, as shown with a solid line and a dotted line shown in FIG. 2, the X-ray tube 30 rotates at high speed along a direction of an arrow AR (channel direction) and irradiates X-rays to the subject S, and then the X-ray detector 40 detects the X-rays.

The X-ray tube 30 can be a structure that a housing contains a cathode sleeve and a target electrode supported in opposed position of the cathode sleeve in X-axis direction. The target electrode comprises disk-shaped tungsten, for example. The target electrode is a rotary type that rotates about an axis and also a reflection type that generates X-rays on the same surface that an electron beam collides.

The X-ray detector 40 has a collimator 20 and a plurality of X-ray detection elements 50 for detecting X-rays. The collimator 20 has a plurality of collimator modules 10 for collimating X-rays from the X-ray tube 30 and an arc-shaped base 60 fixing the plurality of the collimator modules 10 in reference positions. One X-ray detection element 50 is fixed to one collimator module 10 at the opposite side of the X-ray tube 30 so as to be situated between the X-ray tube 30 and the collimator module 10. That means, a plurality of X-ray detection elements 50 are arrayed on XY surfaces of the collimator module 10 along the channel direction. Then, the X-ray detection element 50 detects the X-rays passed through the subject S, which is put on the cradle 120 and carried to the bore 104.

The X-ray detection element 50 has a photodiode chip (not shown) having photoelectric conversion devices arrayed in the channel direction and a slicing direction and a scintillator block (not shown) that emits visible light by receiving X-rays. The X-ray detection element 50 further comprises a semiconductor chip (not shown) having functions to estimate outputs from the photodiode chip and to switch outputs for changing a slicing thickness.

The X-ray CT device 100 further includes an X-ray controller for controlling a width of X-ray beams from the X-ray tube 30 and a rotation controller for controlling rotations of the X-ray tube 30 and the X-ray detector 40.

Overview of Collimator 20

Figure 3:
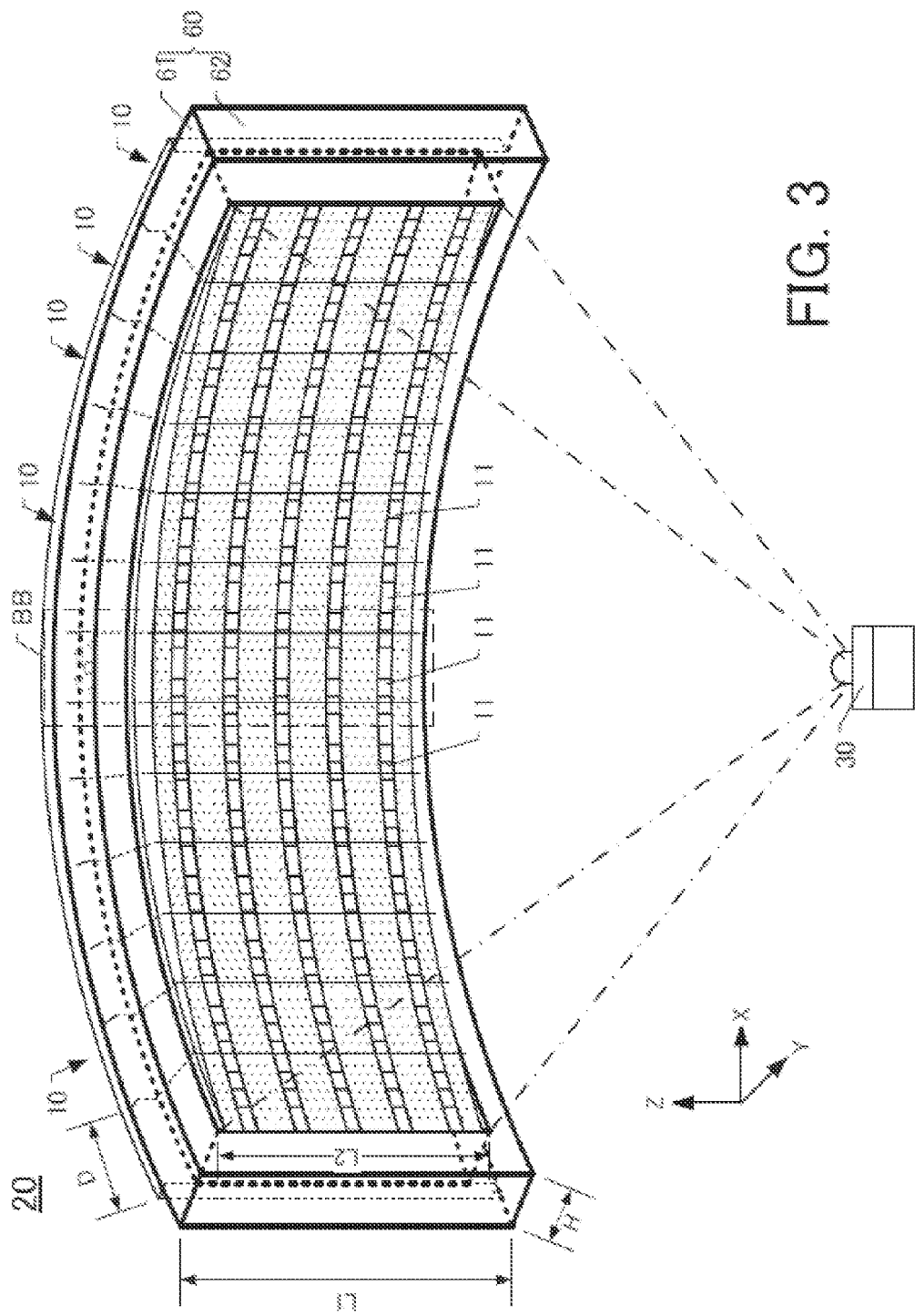
FIG. 3 is a perspective view for explaining a configuration of the collimator 20.

FIG. 3 is a perspective view for explaining a configuration of the collimator 20. As shown in FIG. 3, the collimator 20 includes a plurality of collimator modules 10 for collimating X-rays from the X-ray tube 30 and an arc-shaped base 60 for fixing the plurality of collimator modules 10 in reference positions. For convenience of explanation the X-ray tube 30 is illustrated, but it is not included in the collimator 20.

The base 60 includes a rectangular frame having a pair of circular-arc base members 61 and a pair of linear base members 62 connecting the distal ends of the base members 61. Also positioning pins or positioning holes on the base side for positioning the plurality of collimator modules 10 are provided on the base member 61. In FIG. 3, although the positioning pins or holes are illustrated only on the base side at the reference position corresponding to the collimator module 10 which is surrounded by a dotted line BB, the positioning pins or holes are formed on all reference positions corresponding to collimator modules 10.

At the base 60, a length L1 is in a range of 350 mm to 400 mm for example, a thickness H is about in a range of 35 mm to 40 mm, and a length L2 comprising the base members 61 and 62 is in about a range of 300 mm to 350 mm. A width D of each collimator module 10 is 50 mm, for example. The collimator module 10 will be described below by referring FIG. 4.

For a material of the base 60, a carbon fiber reinforced plastic (CFRP) which is a composite material of aluminum alloy or carbon fiber and a thermoset resin is used because aluminum alloy or CFRP is light in weight and strong, and also has a characteristic of high durability. Because of the light weight and a strong characteristic of aluminum alloy or CFRP, the base 60 can be rotated at high speed in the scanning gantry 101 of the X-ray CT device 100 without generating unnecessary centrifugal forces. Additionally, because of the high durability of aluminum alloy or CFRP, the base 60 hardly strain or bend and so do the collimator modules 10 fixed thereon.

In FIG. 3, thirteen collimator modules 10 are fixed to one base 60, but dozens of collimator modules 10 are fixed for an actual usage. The collimator module 10 has a plurality of collimator single plates 11, which collimates X-ray beams from the X-ray tube 30. Note that this application discloses a first collimator module 10A through a fifth collimator module 10E as the collimator module 10. The collimator module 10 illustrated in FIG. 3 is a second collimator module 10B which will be described by referring FIG. 8 later on.

Overview of Collimator Module 10

First Embodiment

Figure 4B:
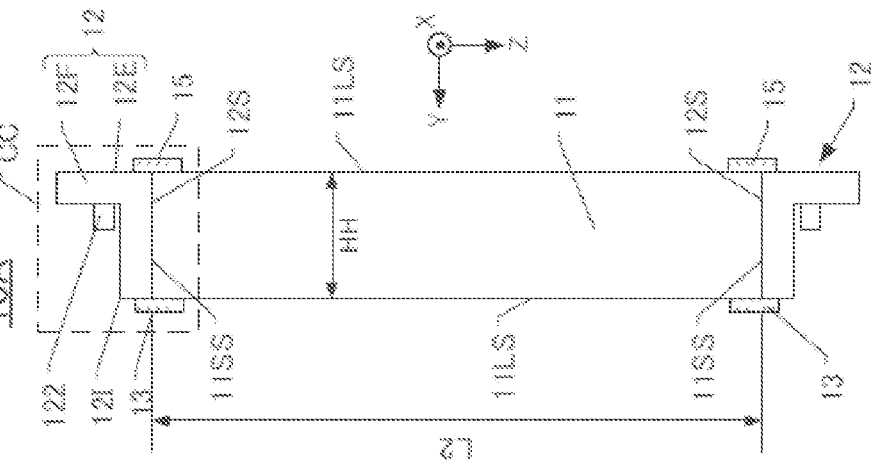
FIG. 4B is a side view of the first collimator module 10A.
Figure 4A:
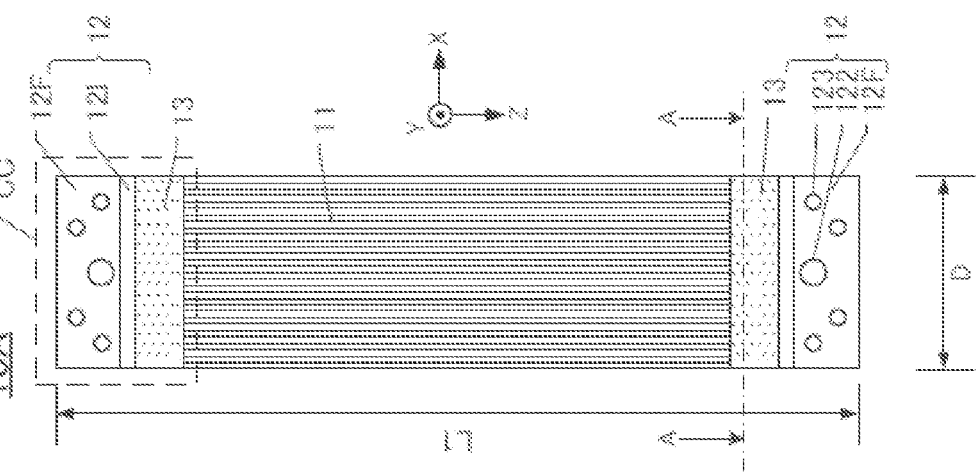
FIG. 4A is a plan view of the first collimator module 10A.

FIGS. 4A and 4B show the first collimator module 10A of a first embodiment. FIG. 4A is a plan view of the first collimator module 10A. FIG. 4B is a side view of the first collimator module 10A.

As shown in FIGS. 4A and 4B, the first collimator module 10A includes dozens of rectangle collimator single plates 11, a pair of blocks 12 formed at both distal ends in Z-axis direction of the collimator single plate 11, and a first incident side fixing sheet 13 and a first emission side fixing sheet 15 formed at both distal ends of the collimator single plate 11 and the blocks 12. In the first embodiment, the collimator single plate 11 is bonded to the blocks 12 by an adhesive, and the first incident side fixing sheet 13 and the first emission side fixing sheet 15 are bonded to the collimator single plate 11 and the blocks 12 by an adhesive. The bonding manner will be explained later by referring FIG. 12.

The first collimator module 10A has a size to be placed on the base 60 shown in FIG. 3. That is, a total length L1 in Z-axis direction of the first collimator module 10A is about 350 mm, which is the same length of the length L1 of the base 60, a thickness in Y-axis direction of the first collimator module 10A is about 30 mm, which is the same thickness of the thickness H of the base 60, and a width D in X-axis direction of the first collimator module 10A is about 50 mm.

A length of long sides of the collimator single plate 11 is about 300 mm and is almost the same length of the length L2 of the inner space of the base 60, and a length HH of short sides of the collimator single plate 11 is about 30 mm and is slightly longer than a thickness WW (see FIG. 7) of the block 12. The collimator single plate 11 is a rectangle shape comprising a pair of long sides 11LS and a pair of short sides 11SS, and the four corners preferably are chamfered or round chamfered. Note that a board thickness t1 (see FIG. 5 and FIG. 6) of the collimator single plate 11 is about 0.2 mm.

The collimator single plate 11 is made of a heavy metal having a high X-ray absorption rate, e.g., molybdenum, tungsten, or lead. When the first collimator module 10A is attached to the base 60 shown in FIG. 3, the X-ray tube 30 is positioned on the extensions of the short side of the collimator single plate 11. Also, the extensions of the long side of the collimator single plate 11 are parallel to the body axis of the subject S, which is the slicing direction.

The block 12 is made of a plastic or a light-weight metal such as aluminum, and the block 12 has an incident side surface 12I and an emission side surface 12E contacting to the base 60. +Y side is a side facing the X-ray tube 30 and X-rays entered from +Y side travels to −Y side. A plurality of first grooves 125 (see FIG. 5) extending from the incident side surface 12I to the emission side surface 12E is formed on the surfaces 12S facing one another. The block 12 further comprises a flange 12F, so it is like a shape of letter "L" when it is seen from X-axis direction. Also, a hole is formed on the flange 12F of the block 12 for inserting a positioning pin 122 to fix the block 12 at a reference position of the base 60.

Figure 5:
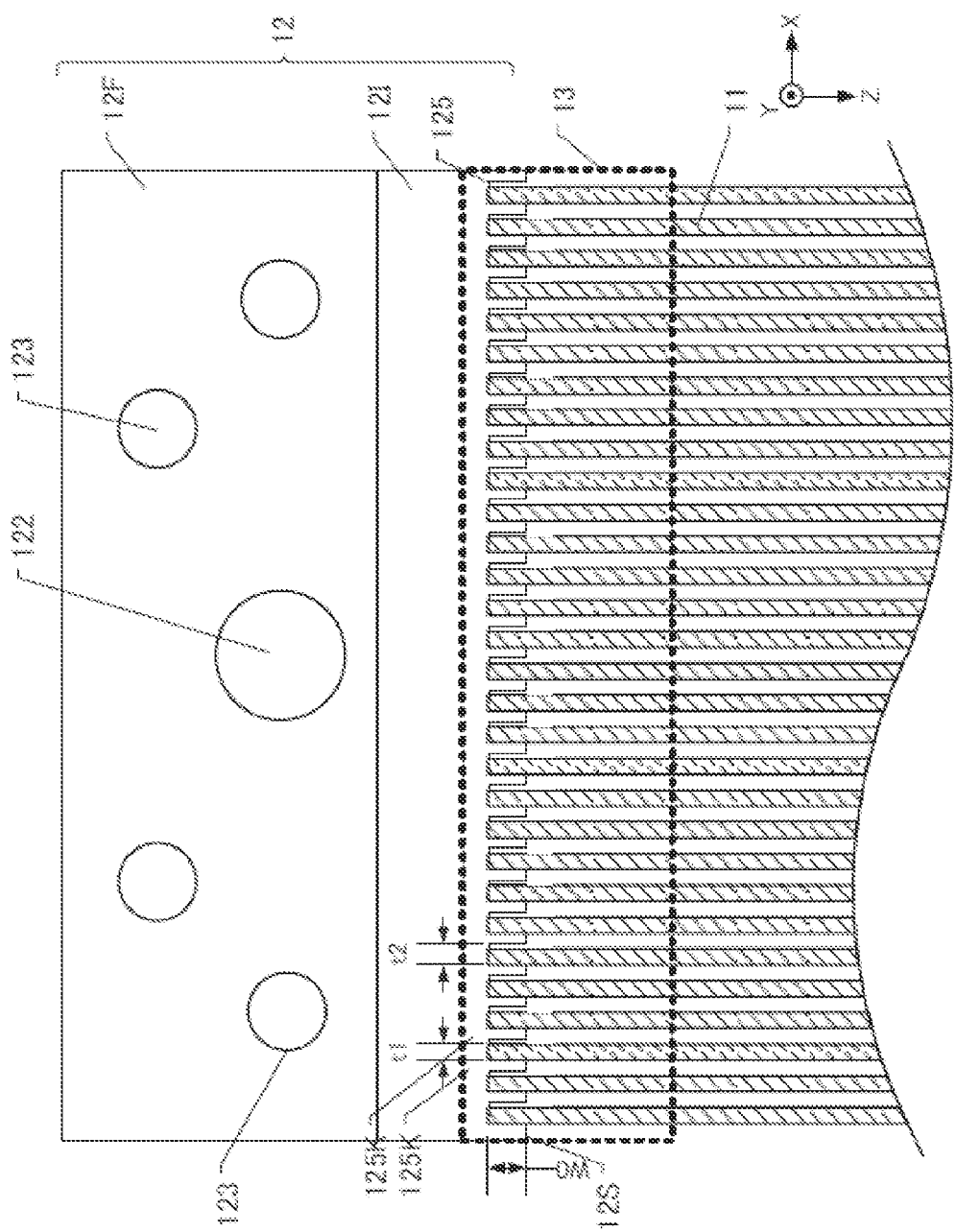
FIG. 5 is an enlarged view of a part surrounding a dotted line CC of FIG. 4A.

Next, the block 12 is described by referring FIG. 5.

FIG. 5 is an enlarged view of a part surrounding a dotted line CC of FIG. 4A. For a better understanding, twenty four collimator single plates 11 are illustrated in FIG. 5, but the fist collimator module 10A actually has dozens of them. For showing the first grooves 125, the first incident side fixing sheet 13 is illustrated transparent (and it is shown with a dotted line).

As shown in FIG. 5, dozens of first grooves 125 corresponding to dozens of collimator single plates 11 are formed on the block 12. A width t2 in X-axis direction of the first groove 125 is formed wider than a width t1 of the collimator single plate 11 for inserting the collimator single plate 11 into the first groove 125 and the width t2 is 0.24 mm, for example. Thus, the short side 11SS of the collimator single plate 11 is inserted easily into the first groove 125. In the first embodiment, a depth W0 of the first groove 125 into which the collimator single plate 11 is inserted is 1.0 mm, for example. A side surface 125K in a −X direction of the first groove 125 of the block 12 is formed at a precise position corresponding to the position of the positioning pin 122. Thus, if the base block 12 is fixed to the right position of the base 60, the collimator single plate 11 is touched to the side surface 125K firmly so that a plurality of collimator single plates 11 are positioned at right positions.

The first groove 125 is formed from the incident side surface 12I to the emission side surface 12E and it spreads like a fan shape when it is seen from Z-axis direction. That is, when the first collimator module 10A is attached to the base 60 shown in FIG. 3, the X-ray tube 30 is positioned on the extensions of the short side of the collimator single plate 11.

Further, a hole is formed at the center of the flange 12F of the block 12 and a positioning pin 122 is inserted into the hole. This positioning pin 122 is for positioning and placing the collimator module 10 at the reference position of the base 60 as explained by referring FIG. 3. Four positioning holes 123 are formed around the positioning pin 122. Those four positioning holes 123 are configured to fix the X-ray detection element 50 shown in FIG. 2 to a right position.

Figure 6A:
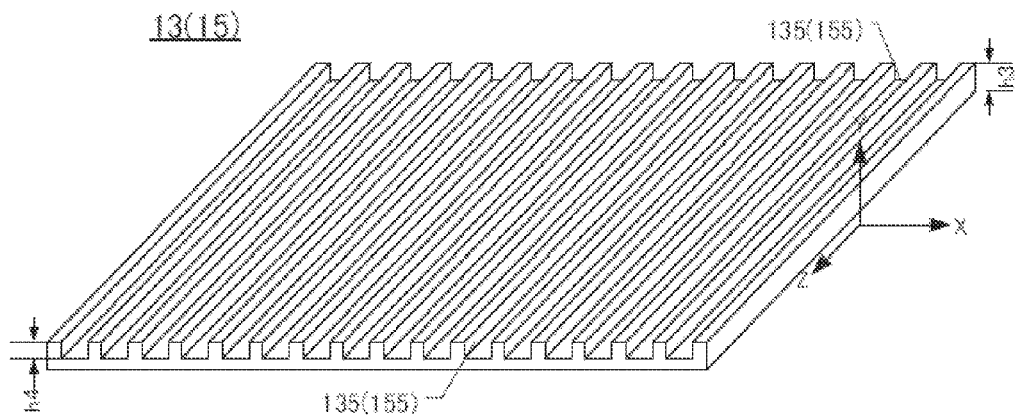
FIG. 6A is a perspective view of the first incident side fixing sheet 13 and the first emission side fixing sheet 15.
Figure 6B:
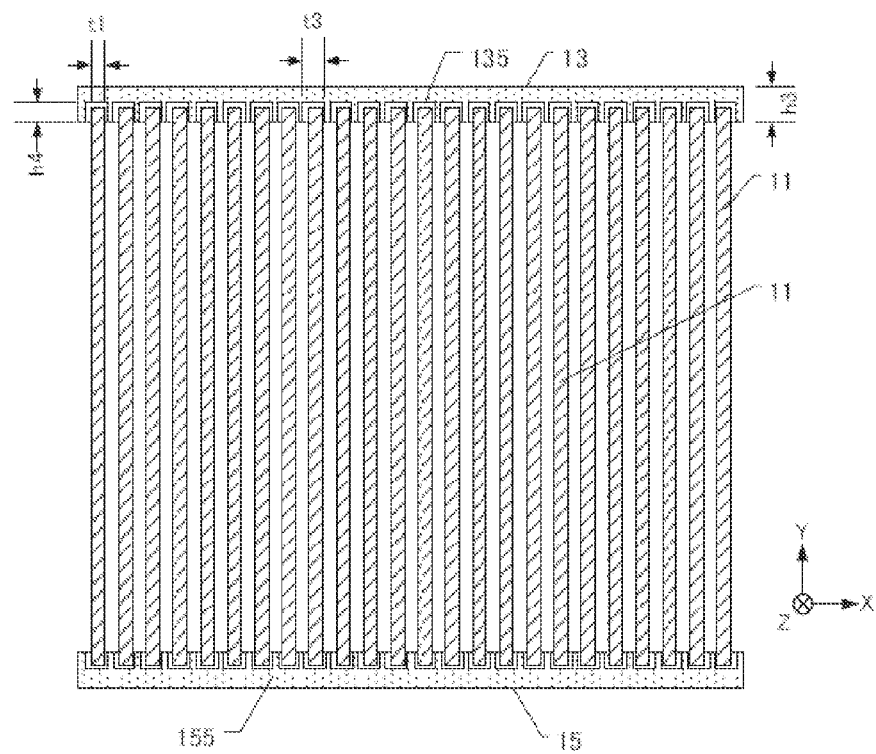
FIG. 6B is a cross-sectional view along A-A line of FIG. 4A where the first incident side fixing sheet 13 and the first emission side fixing sheet 15 are bonded to the collimator single plate 11 by an adhesive.
Figure 7:
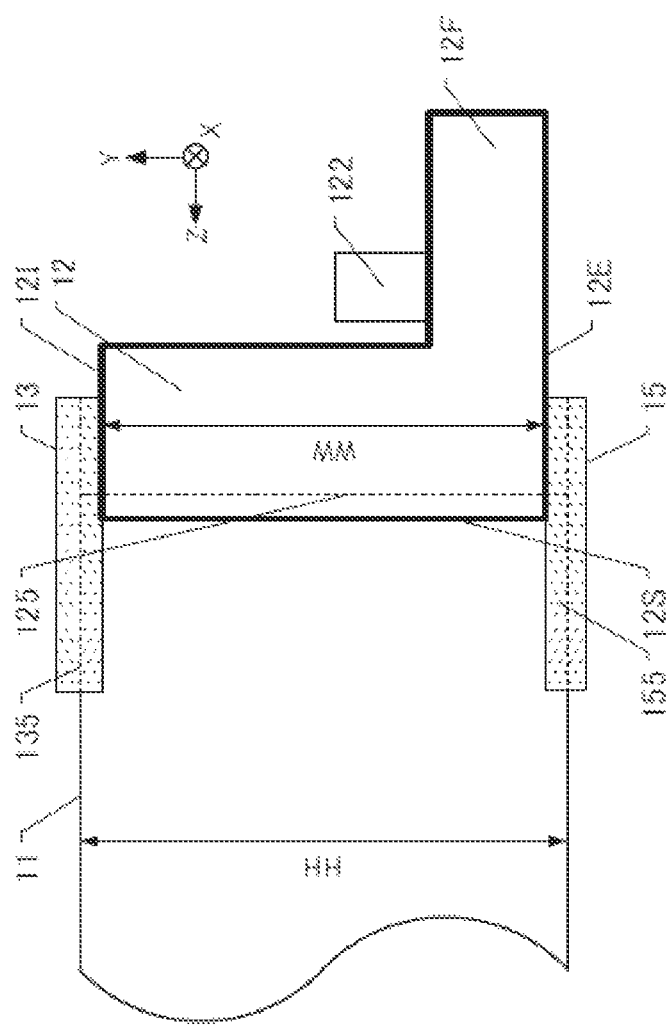
FIG. 7 is a partial enlarged view of an area surrounded by a dotted line CC of FIG. 4B.

Next, the first incident side fixing sheet 13 and the first emission side fixing sheet 15 are explained by referring FIG. 6 and FIG. 7. FIGS. 6A and 6B is a figure for explaining the first incident side fixing sheet 13 and the first emission side fixing sheet 15. FIG. 6A is a perspective view of the first incident side fixing sheet 13 and the first emission side fixing sheet 15. FIG. 6B is a cross-sectional view along A-A line of FIG. 4A where the first incident side fixing sheet 13 and the first emission side fixing sheet 15 are bonded to the collimator single plate 11 by an adhesive (not shown).

As shown in FIG. 6A, a plurality of second grooves 135 are formed parallel to one another on one surface of the first incident side fixing sheet 13. A plurality of second grooves 155 are formed on one surface of the first emission side fixing sheet 15 in the same fashion. In the first embodiment, the pitch of the second grooves 135 and the second grooves 155 is formed so as to be the same pitch of the first grooves 125 of the block 12 explained by referring FIG. 5. A thickness h3 of the first incident side fixing sheet 13 and the first emission side fixing sheet 15 is about in a range of 0.2 mm to 0.5 mm, and a depth h4 of the second groove 135 and 155 is in a range of 0.1 mm to 0.3 mm. Note that the second grooves 135 on the first incident side fixing sheet 13 and the second grooves 155 on the first emission side fixing sheet 15 are formed depending on the number of collimator single plates 11. Further, the first incident side fixing sheet 13 is situated on a side where X-rays come in, and the first emission side fixing sheet 15 is situated on a side where X-rays emit. For the first incident side fixing sheet 13 and the first emission side fixing sheet 15, carbon fiber reinforced plastic (CFRP) having X-ray transmission property is used.

The long sides 11LS, which is a side X-rays come in (+Y side in FIG. 6B), of the collimator single plates 11 are inserted into the second grooves 135 of the first incident side fixing sheet 13 and bonded by an adhesive. Also, the long sides 11LS, which is a side X-rays emit (−Y side in FIG. 6N), of the collimator single plates 11 are inserted into the second grooves 155 of the first emission side fixing sheet 15 and bonded by an adhesive. As shown in FIG. 6B, a width t3 of the second grooves 135 and 155 is wider than a width t1 of the collimator single plate 11 so that respective long sides 11LS of the collimator single plates 11 can be easily inserted into the second grooves 135 and 155.

FIG. 7 is a partial enlarged view of an area surrounded by a dotted line CC of FIG. 4B. As shown in FIG. 7, the short side 11SS of the collimator single plate 11 is inserted into the first groove 125 of the block 12 and the long side 11LS of the collimator single plate 11 is inserted into the second groove 135 of the first incident side fixing sheet 13 and the second groove 155 of the first emission side fixing sheet 15. The short side 11SS of the collimator single plate 11 is fixed to the first groove 125 by an adhesive, and a portion of each of the long sides 11LS of the collimator single plate 11 is fixed to the second grooves 135 and 155 by an adhesive as well.

Note that a width HH of the collimator single plate 11 is wider than a thickness WW of the bock 12 for the depth of the second grooves 135 and 155 (h4×2). Parts of the first incident side fixing sheet 13 other than the second grooves 135 are fixed to the incident-side surface 12I of the block 12 by an adhesive. Also, parts of the first emission side fixing sheet 15 other than the second grooves 155 are fixed to the emission-side surface 12E of the block 12 by an adhesive.

As a result, the short side 11SS of the collimator single plate 11 is firmly fixed to the first groove 125 of the block 12. Also, a portion of the long side 11LS adjacent to the short side 11SS is fixed to the block 12 by the first incident side fixing sheet 13 and the first emission side fixing sheet 15. Further, as shown in FIG. 5, the collimator single plate 11 is precisely positioned on the wall surface of the first groove 125K in −X direction.

According to the collimator module of the first embodiment, in a condition that the short sides 11SS are inserted into the first grooves 125 and the long sides 11LS are inserted into the second grooves 135, the first grooves 125 of the block 12 and the portions of the collimator single plate 11 adjacent to the first grooves 125 are covered at four places by the first incident side fixing sheet 13 and the first emission side fixing sheet 15 respectively. Therefore, dozens of the collimator single plates 11 hardly bend even they are arrayed in more than a line of 300 mm in a long side direction when the X-ray detector 40 having the first collimator module 10A rotates at high speed. Then, the collimator single plate 11 collimates X-ray beams from the X-ray tube 30 accurately.

Note that in the collimator module of the first embodiment, only some portions of the long side 11LS of the collimator single plate 11 are covered by the first incident side fixing sheet 13 and the first emission side fixing sheet 15, but entire portion of the long side 11LS can be covered.

Second Embodiment

Figure 8A:
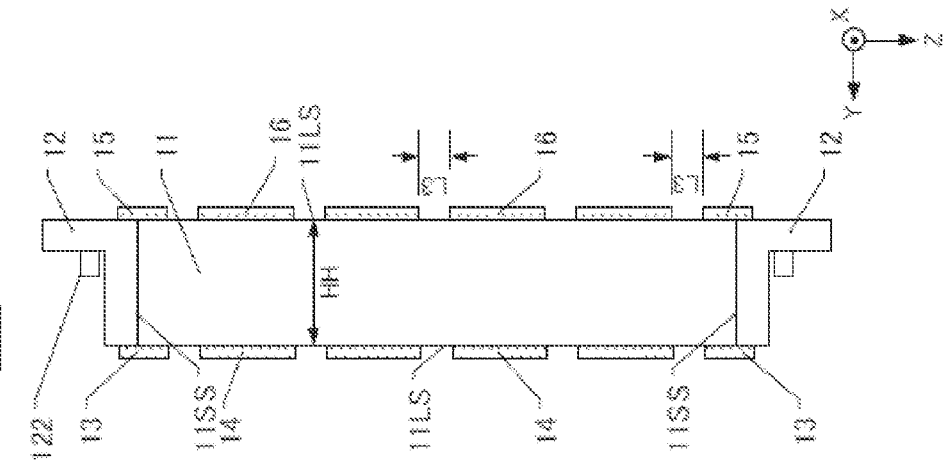
FIG. 8A is a flat view of the second collimator module 10B.
Figure 8B:
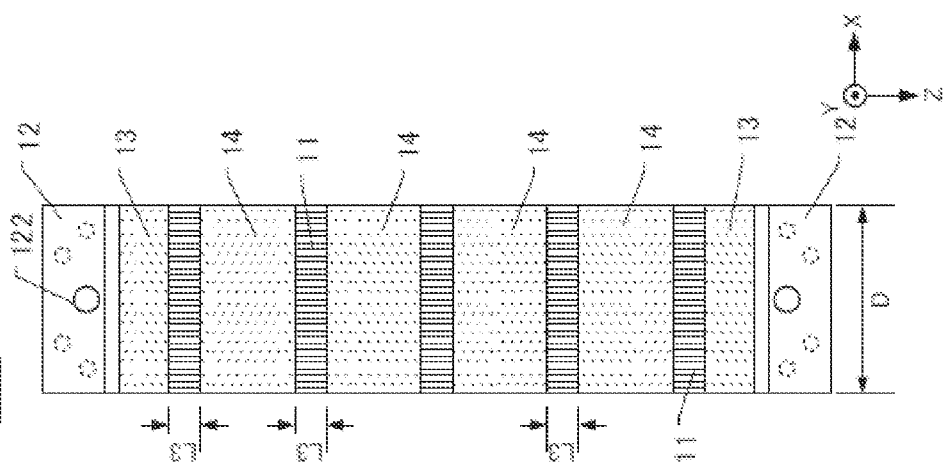
FIG. 8B is a side view of the second collimator module 10B.

FIGS. 8A and 8B are figures for explaining a second collimator module 10B of a second embodiment. FIG. 8A is a flat view of the second collimator module 10B. FIG. 8B is a side view of the second collimator module 10B.

As shown in FIGS. 8A and 8B, the second collimator module 10B has a configuration that four second incident side fixing sheets 14 and four second emission side fixing sheets 16 are fixed in addition to the first collimator module 10A of the first embodiment. Thus, the second collimator module 10B has the same configuration of the first embodiment except the second incident side fixing sheets 14 and the second emission side fixing sheets 16.

On respective one surfaces of the second incident side fixing sheet 14 and the second emission side fixing sheet 16, dozens of second grooves are formed with designated pitches respectively same as the first incident side fixing sheet 13 and the first emission side fixing sheet 15. For the second incident side fixing sheet 14 and the second emission side fixing sheet 16, carbon fiber reinforced plastic (CFRP) having X-ray transmission property is also used.

The second incident side fixing sheet 14 that only bonds to the long side 11LS of the collimator single plate 11 is arranged on a side of the collimator single plate 11 where X-ray beams come in (+Y side). The second emission side fixing sheet 16 that only bonds to the long side 11LS of the collimator single plate 11 is arranged on another side of the collimator single plate 11 where X-ray beams exit (−Y side).

A space having a distance L3 is maintained between the first incident side fixing sheet 13 and the second incident side fixing sheet 14. The space (distance L3) is also maintained between adjacent second incident side fixing sheets 14, between the first emission side fixing sheet 15 and the second emission side fixing sheet 16, and between adjacent second emission side fixing sheets 16. The space (distance L3) corresponds to the pressing components 75 (see FIGS. 12 and 13) arraying a plurality of collimator single plates 11.

According to the collimator module of the second embodiment, the first groove 125 of the block 12 and the portions of the collimator single plate 11 adjacent to the first groove 125 are covered at four places by the first incident side fixing sheet 13 and the first emission side fixing sheet 15 respectively when the short sides 11SS are inserted into the first grooves 125 and the long sides 11LS are inserted into the second grooves 135. And the second incident side fixing sheet 14 and the second emission side fixing sheet 16 further cover the long sides 11LS of the collimator single plates 11. Therefore, dozens of the collimator single plates 11 hardly bend even they are arrayed in more than a line of 300 mm in a long side direction when the X-ray detector 40 having the second collimator module 10B rotates at high speed. Then, the collimator single plate 11 collimates X-ray beams from the X-ray tube 30 accurately.

Moreover, according to the collimator module of the second embodiment, a space (L3) is maintained between the first incident side fixing sheet 13 and the second incident side fixing sheet 14, between adjacent second fixing sheets on incident side 14, between the first emission side fixing sheet 15 and the second emission side fixing sheet 16, and between adjacent second emission side fixing sheets 16. Therefore, in the manufacturing process, a jig (i.e. pressing components 75 shown in FIG. 12 and FIG. 13) for arraying a plurality of the collimator single plates is inserted into the spaces to array the collimator single plates with a high degree of accuracy. Further, the collimator single plates can be observed or inspected by an imaging camera through the spaces to determine whether the collimator single plates are arrayed correctly.

Third Embodiment

FIG. 9 is a figure for explaining a third collimator module 10C of the third embodiment. FIG. 9A is a flat view of the third collimator module 10C. FIG. 9B is a side view of the third collimator module 10C.

As shown in FIGS. 9A and 9B, the third collimator module 10C has a configuration that five third fixing sheets on incident side 17 and five third fixing sheets on emission side 19 are fixed in addition to the second collimator module 10B of the second embodiment. Thus, the third collimator module 10C has the same configuration of the second embodiment except the third incident side fixing sheet 17 and the third emission side fixing sheet 19.

The third incident side fixing sheet 17 and the third emission side fixing sheet 19 have dozens of third grooves on one surface with designated pitches respectively same as the first incident side fixing sheet 13 and the first emission side fixing sheet 15. CFRP having X-ray transmission property is also used for the third incident side fixing sheet 17 and the third emission side fixing sheet 19.

As explained in the second embodiment, the space having distance L3 is maintained between the first incident side fixing sheet 13 and the second incident side fixing sheet 14, and also between adjacent second fixing sheets on incident side 14. The fixing sheets on emission side are arranged in the same fashion. The third incident side fixing sheet 17 and the third emission side fixing sheet 19 are fixed so as to fill the spaces (L3).

The third collimator module 10C can fix a plurality of collimator single plates 11 more firmly by bonding the third incident side fixing sheet 17 and the third emission side fixing sheet 19 to the long sides of the collimator single plates 11 of the second collimator module 10B of the second embodiment.

Fourth Embodiment

Figure 10A:
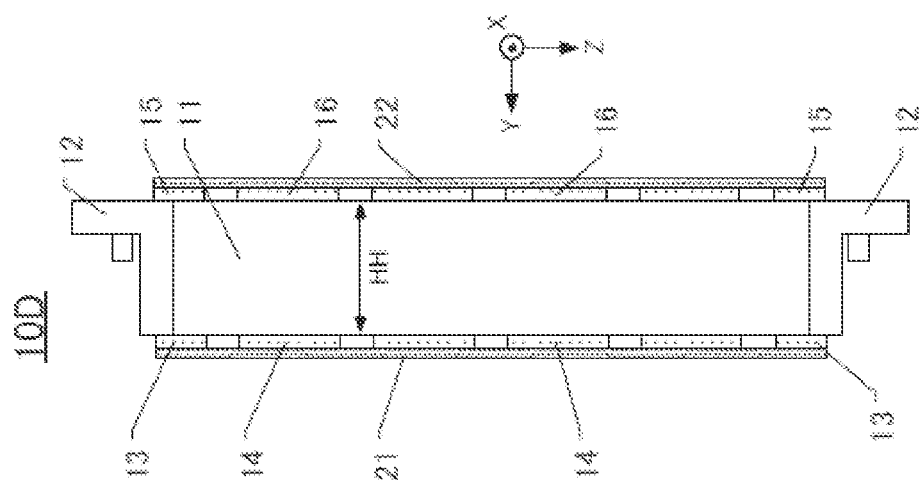
FIG. 10A is a top view of the fourth collimator module 10D.
Figure 10B:
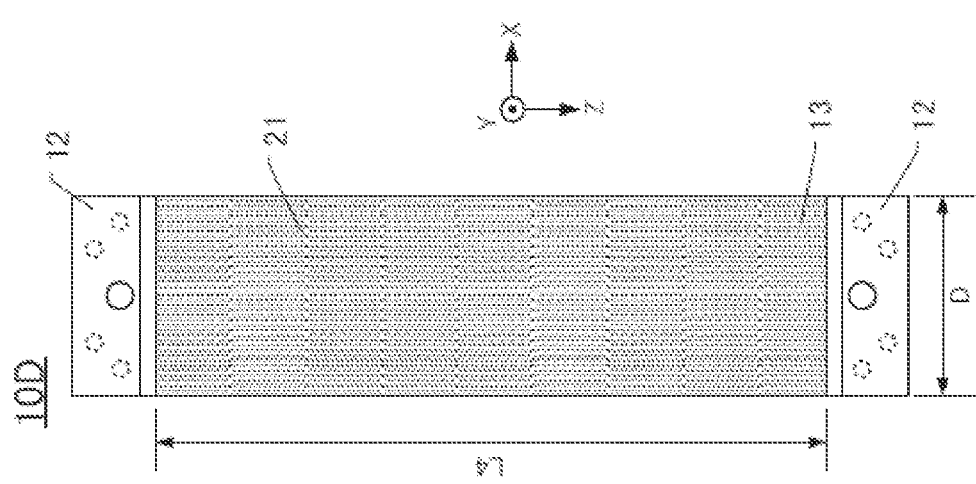
FIG. 10B is a side view of the fourth collimator module 10D.

FIGS. 10A and 10B are figures for explaining a fourth collimator module 10D of the fourth embodiment. FIG. 10A is a top view of the fourth collimator module 10D. FIG. 10B is a side view of the fourth collimator module 10D.

As shown in FIGS. 10A and 10B, the fourth collimator module 10D has a configuration that a supporting sheet on incident side 21 and a supporting sheet on emission side 22 are additionally bonded to the second collimator module 10B of the second embodiment. The fourth collimator module 10D has the same configuration of the second embodiment except the supporting sheet on incident side 21 and the supporting sheet on emission side 22.

CFRP having X-ray transmission property is used for the supporting sheet on incident side 21 and the supporting sheet on emission side 22. The length L4 in Z-axis direction of the incident side supporting sheet 21 and the emission side supporting sheet 22 is about in a range of 310 mm to 360 mm. One incident side supporting sheet 21 is attached to the outer side of the first incident side fixing sheet 13 and the second incident side fixing sheet 14 so as to cover entire outer surface of the first incident side fixing sheet 13 and the second incident side fixing sheet 14. One emission side supporting sheet 22 is also attached to the outer side of the first emission side fixing sheet 15 and the second emission side fixing sheet 16 so as to cover entire outer surface of the first emission side fixing sheet 15 and the second emission side fixing sheet 16.

The incident side supporting sheet 21 and the emission side supporting sheet 22 do not touch the long sides 11LS of a plurality of the collimator single plates 11. Therefore, the incident side supporting sheet 21 and the emission side supporting sheet 22 may have or may not have the second grooves 135 and 155.

By fixing the supporting sheet on incident side 21 and the supporting sheet on emission side 22 at the incident side and the emission side further, the forth collimator module 10D can fix the collimator single plates 11 more firmly.

It is not particularly shown, but the second collimator module 10B on which either the supporting sheet on incident side 21 or the supporting sheet on emission side 22 is attached can be provided.

Fifth Embodiment

Figure 11A:
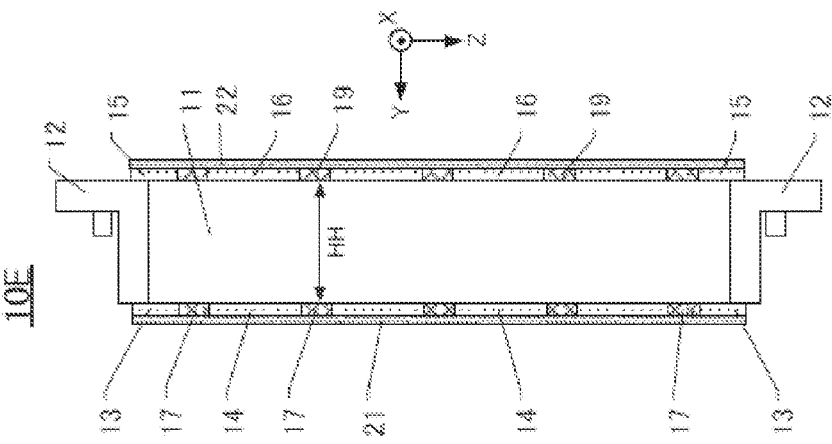
FIG. 11A is a top view of the fifth collimator module 10E.
Figure 11B:
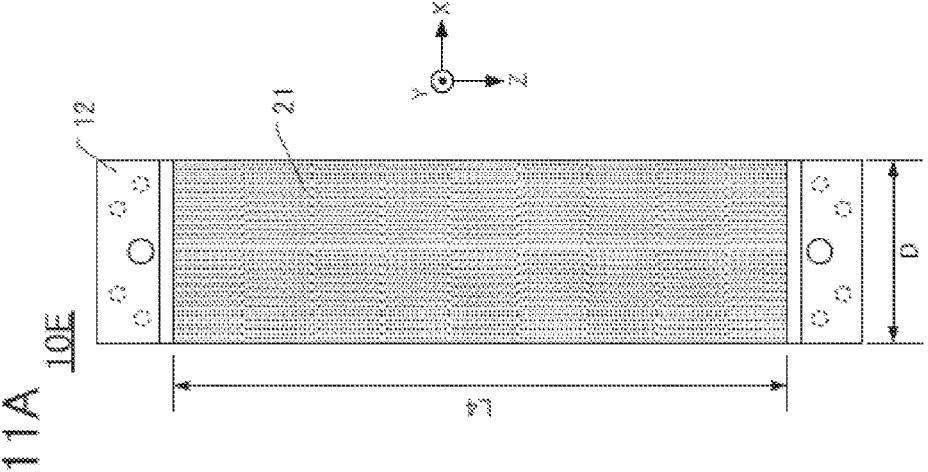
FIG. 11B is a side view of the fifth collimator module 10E.

FIGS. 11A and 11B are figures for explaining a fifth collimator module 11E of the fifth embodiment. FIG. 11A is a top view of the fifth collimator module 10E. FIG. 11B is a side view of the fifth collimator module 10E.

As shown in FIG. 11, the fifth collimator module 10E has a configuration that the incident side supporting sheet 21 and the emission side supporting sheet 22 are further attached to the third collimator module 10C of the third embodiment. The fifth collimator module 10E has the same configuration of the third embodiment except the incident side supporting sheet 21 and the emission side supporting sheet 22. In the third embodiment, the third incident side fixing sheets 17 are fixed to spaces between the first incident side fixing sheet 13 and the second incident side fixing sheet 14, and between adjacent second incident side fixing sheets 14. The incident side supporting sheet 21 is attached so as to cover the first incident side fixing sheet 13, the second incident side fixing sheet 14, and the third incident side fixing sheet 17. It is not particularly shown, but the emission side is in the same fashion.

By fixing the supporting sheet on incident side 21 and the supporting sheet on emission side 22 to the third collimator module 10C of the third embodiment further, the fifth collimator module 10E can fix the collimator single plates 11 more firmly.

It is not particularly shown, but the third collimator module 10C on which either the incident side supporting sheet 21 or the emission side supporting sheet 22 is attached can be provided.

Assembling Processes of Collimator Module 10

Next, assembling processes of the collimator module 10 is explained. First of all, a jig 10 used for assembling the collimator module 10 is explained by referring FIG. 12 through FIG. 14.

Figure 12:
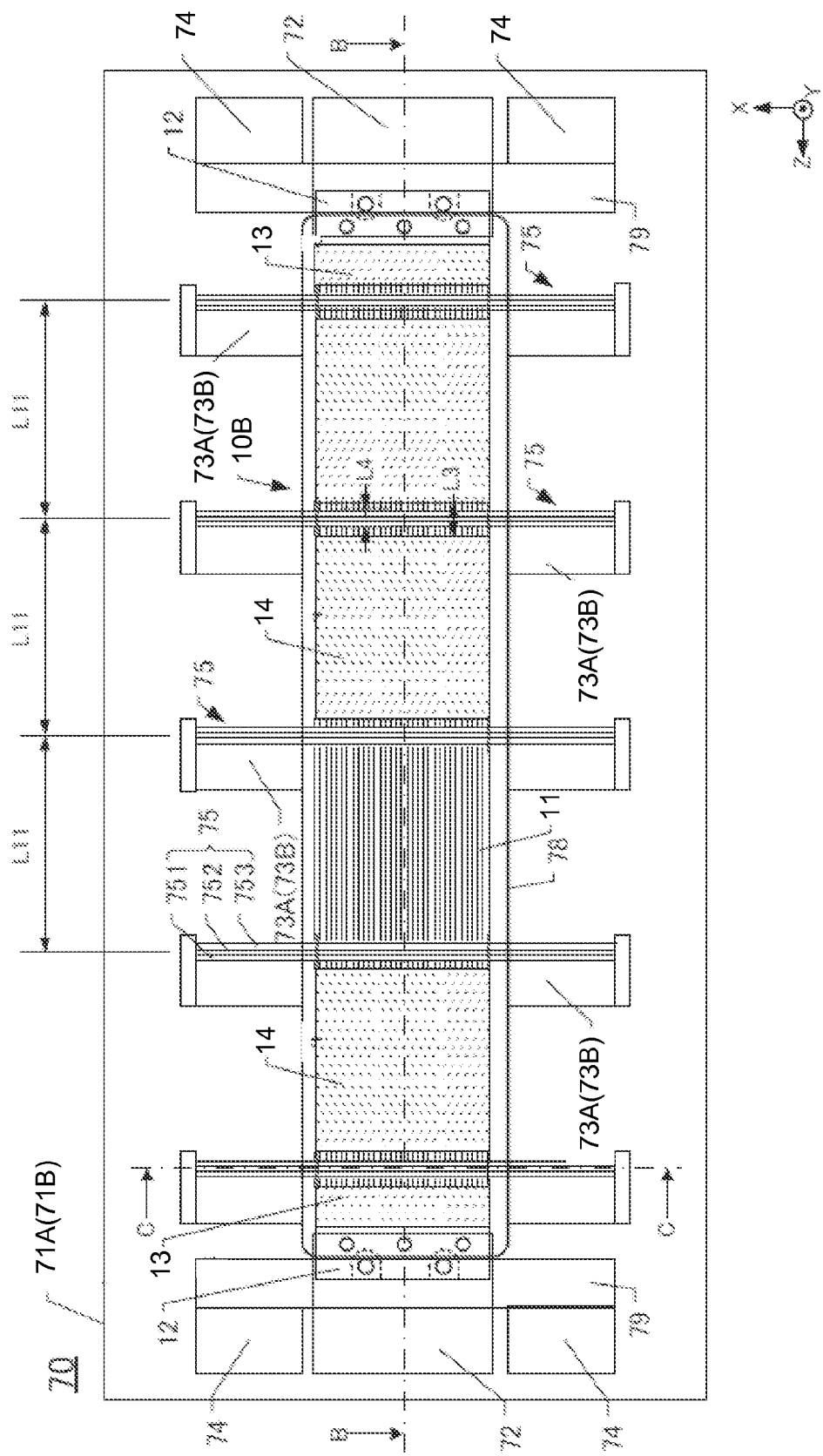
FIG. 12 is a flat view of the jig 70 (including a lower jig 10A and an upper jig 70B) for assembling the collimator module 10.
Figure 13:
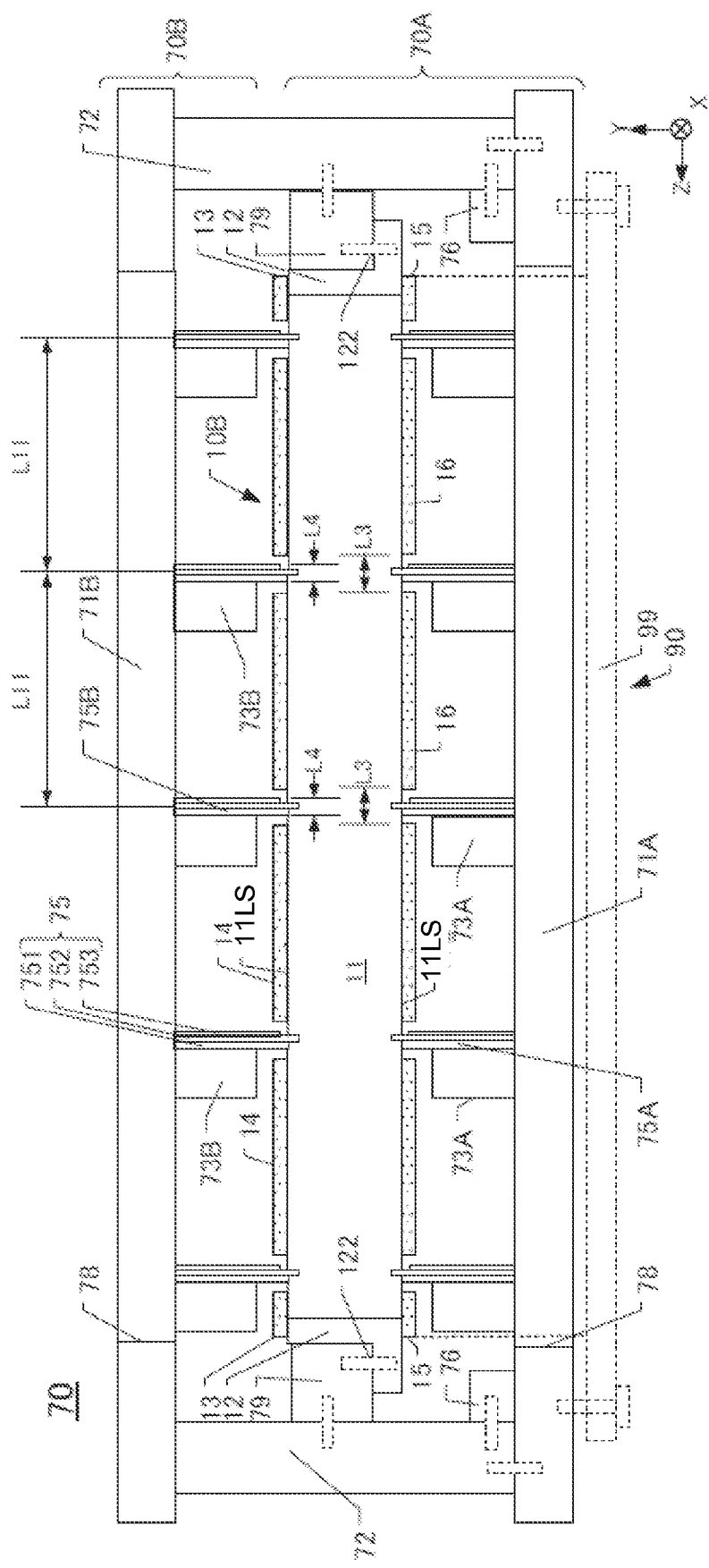
FIG. 13 is a cross-sectional side view along the B-B line of the jig 70 shown in FIG. 12.

FIG. 12 is a flat view of the jig 70 (including a lower jig 70A and an upper jig 70B) for assembling the collimator module 10. The upper jig 70B is not illustrated for an explanation. In FIG. 12 and FIG. 13, the assembling steps of the second collimator module 10B explained in the second embodiment is explained. Thus, the first incident side fixing sheets 13 and the second incident side fixing sheets 14 are fixed to a plurality of collimator single plates 11 of the second collimator module 10B. However in FIG. 12, one of the second incident side fixing sheet 14 is removed for making the collimator single plate 11 more visible.

As shown in FIG. 13, the jig 70 has the lower jig 70A and the upper jig 70B. A pair of pillar mounts 72, connecting pillars 74, and a pair of collimator module fixing blocks 79 that are explained later are attached to the lower jig 70A, which is the only difference between the lower jig 70A and the upper jig 70B. Now the lower jig 70A is mainly used for explanation. For members shown in FIG. 12, FIG. 13, and FIG. 17, "A" is suffixed to numberings of lower members and "B" is suffixed to numberings of upper members for distinguishing.

The lower jig 70A has a frame 70 having a penetrating portion 78 formed at the center. A supporting block 90 explained by referring FIG. 15 is inserted into the penetrating portion 78. In FIG. 13, the supporting block 90 is shown with dotted lines. Five pairs of blocks for pressing component 73A are placed in X-axis direction on the upper surface of the frame 71. One pair of blocks for pressing component 73A positions one pressing component 75. The pressing component 75 lying next to each other are arrayed in Z-axis direction at a distance L11, such as 50 mm. The pressing components 75 align a plurality of collimator single plates 11 extending in Z-axis direction. The pressing component 75 has a reference board 751, a comb-shaped member 752, and a spring board member 753. The pressing component 75 has a width L4 in Z-axis direction. The width L4 of the pressing component 75 is narrower than the space L3 between the first incident side fixing sheet 13 and the second incident side fixing sheet 14, or between adjacent second incident side fixing sheets 14. This is because, in a condition that the pressing components 75 have aligned a plurality of collimator single plates 11, the first incident side fixing sheet 13 and the second incident side fixing sheet 14 are fixed at positions where the pressing components 75 are not arranged.

A pair of pillar mounts 72 is formed at both distal ends in Z-axis direction on the upper surface of the frame 71. A space between the pair of pillar mounts 72 is longer than the entire length L1 in Z-axis direction of the second collimator module 10B. The pair of pillar mounts 72 is positioned by a pair of mounting blocks 76 (see FIG. 13) and positioning pins formed on the frame 71. Further, a pair of collimator module fixing blocks 79 are positioned and placed by the positioning pins on the pair of pillar mounts 72 inwardly. A pair of the blocks 12 of the second collimator module 10 is fixed to the collimator module fixing blocks 79. The pair of blocks 12 is correctly positioned to the collimator module fixing blocks 79 by the positioning pins 122 shown in FIG. 8.

Four connecting pillars 74 are formed at four corners on the lower jig 70A of the jig 70 to support the upper jig 70B having the same configuration of the lower jig 70A. During assembling of the second collimator module 10B, the pair of pillar mounts 72 and the pair of collimator module blocks 79 are removed from the pair of blocks 12 in turn (this will be explained with a flow chart of FIG. 16). Therefore, the pillar mount 72 is formed about 0.1 mm to 3 mm shorter in Y-axis direction than the connecting pillar 74.

Figure 14A:
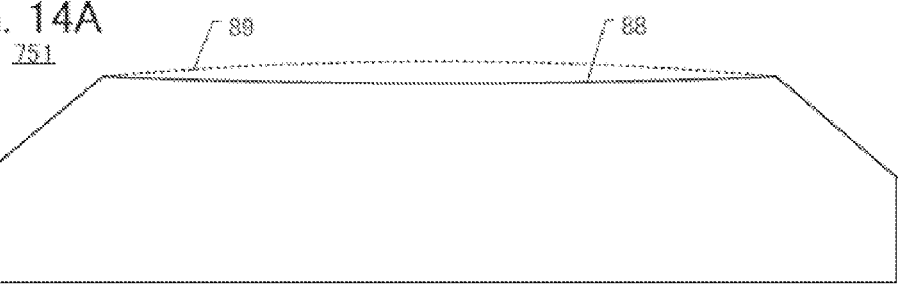
FIG. 14A is a front view of the reference board 751.
Figure 14B:
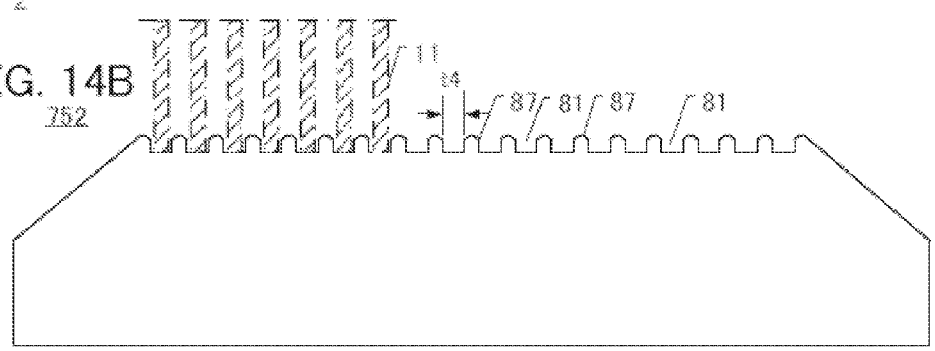
FIG. 14B is a front view of the comb-shaped member 752.
Figure 14C:
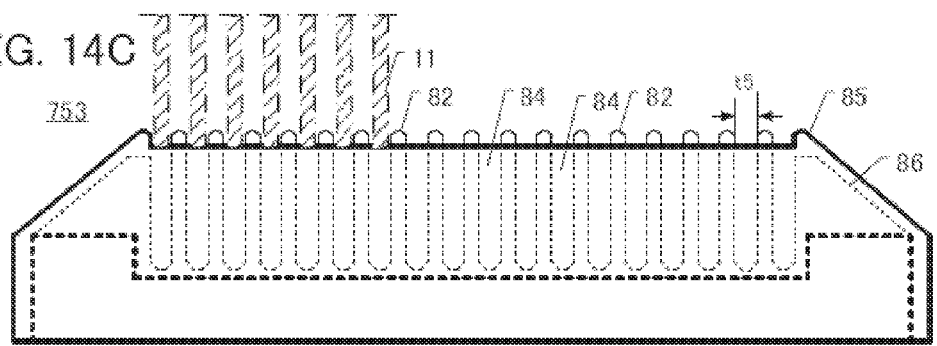
FIG. 14C is a front view of the spring board member 753.

The pressing component 75 is explained by referring FIGS. 14A, 14B and 14C.

FIGS. 14A, 14B and 14C are figures showing the configuration of the pressing component 75. As shown in FIG. 12 and FIG. 13, the pressing component 75 includes a reference board 751, a comb-shaped member 752, and a spring board member 753. FIG. 14A is a front view of the reference board 751. FIG. 14B is a front view of the comb-shaped member 752. FIG. 14C is a front view of the spring board member 753.

As shown in FIG. 14A, the reference board 751 is nearly a trapezoidal shape and an upper base 88 or an upper base 89 (dotted line) is formed a curved line. The reference board 751 touches the long sides 11LS of a plurality of collimator single plates 11. The reference board 751 of the pressing component 75 arranged on the lower jig 70A is a reference for the collimator single plate 11 on emission side of X-ray beams. Thus, the upper base 88 of the reference board 751 is a concave curved line. On the other hand, the reference board 751 of the pressing component 75 arranged on the upper jig 70B is a reference for the collimator single plate 11 on incident side of X-ray beams. Thus, the upper base 89 of the reference board 751 is a convex curved line. The reference board 751 has a rigidity for contacting the long sides 11LS of a plurality of collimator single plates 11. The reference board 751 is composed mostly of, for example, iron steel, stainless steel, or aluminum alloy, and the thickness is in a range of 0.5 mm to 3.0 mm.

As shown in FIG. 14B, the comb-shaped member 752 is nearly a trapezoidal shape same as the reference board 751. Comb-shaped cutouts 81 into which a plurality of collimator single plates 11 is inserted are formed at the upper base 87. Dozens of cutouts 81 are formed. A width t4 of one cutout 81 is almost the same widths of the width t2 of the first grooves of the block 12 shown in FIG. 5, or the width t3 of the second grooves 135 of the first incident side fixing sheet 13, which is 0.24 mm, for example. The comb-shaped member 752 is made mostly of, for example, iron steel, stainless steel, or aluminum alloy, and the thickness is in a range of 0.5 mm to 3.0 mm.

As shown in FIG. 14C, the spring board member 753 includes a spring portion 82 and a first backing plate 85 and a second backing plate 86. This spring portion 82 is a member for pressing a plurality of collimator single plates 11 in X-axis direction. Thus, cutouts 84 are formed on the spring portion 82 with the same pitch of the comb-shaped member 752, and a width t5 of the cutout 84 is same as the width t4 of the cutout 81. In order for the spring portion 82 to be elastically-deformed easily, a depth of the cutout 84 (Y-axis direction) is deeper than of the cutout 81 of the comb-shaped member 752 and a thickness of the spring portion 82 is in a range of 0.1 mm to 0.5 mm. The spring portion 82 is made of, for example, iron steel for spring, stainless steel for spring, or plastics. Since the thickness of the spring portion 82 is thin, the first backing plate 85 and the second backing plate 86 back the spring portion 82 from both surfaces.

The pressing component 75 is set where a plurality of cutouts 81 of the comb-shaped member 752 and a plurality of cutouts 84 of the spring board member 753 are layered. In the condition that the cutouts 81 and the cutouts 84 are layered, the long sides 11LS of a plurality of collimator single plates 11 are inserted to the cutouts until the long sides 11LS touch the reference board 75. Although FIG. 14 does not show, the spring portion 82 can align a plurality of collimator single plates 11 at a time in X-axis direction by moving the spring board member 753 in X-axis direction with cams or enlarged holes to the comb-shaped member 752.

FIG. 15 shows a supporting block 90 for supporting the collimator single plate 11 when the first incident side fixing sheet 13, the first emission side fixing sheet 15, the second incident side fixing sheet 14, and the second emission side fixing sheet 16 are fixed to the collimator single plate 11. As shown in FIG. 13, the supporting block 90 is attached to the frame 70 of the lower jig 70A. Also, it is not shown in FIG. 13, but when the jig 70 is turned upside down (Y-axis direction), the supporting block 90 is attached to the upper frame 71B of the upper jig 70B.

As shown in FIG. 15, the supporting block 90 includes a first sheet mounting portion 91, a second sheet mounting portion 92, and a base portion 99. The first incident side fixing sheet 13 and the first emission side fixing sheet 15 are mounted on top surfaces 93 of the first sheet mounting portion 91. The second incident side fixing sheet 14 and the second emission side fixing sheet 16 are mounted on top surfaces 93 of the second sheet mounting portion 92. A width W11 of the first sheet mounting portion 91 is formed the same width of or relatively wider than the first incident side fixing sheet 13 and the first emission side fixing sheet 15. A width W12 of the second sheet mounting portion 92 is formed the same width of or relatively wider than the second incident side fixing sheet 14 and the second emission side fixing sheet 16. A width W15 of a concave portion 94 is formed wider than the width L4 of the pressing component 75 such that the first sheet mounting portion 91 and the second sheet mounting portion 92 do not touch the pressing component 75 when the supporting block 90 is attached to the frame 71. The width 15 of the concave portion 94 is nearly the same length or relatively narrower than the space L3 between the first incident side fixing sheet 13 and the second incident side fixing sheet 14, or between adjacent second incident side fixing sheets 14 explained in FIG. 13.

Figure 16:
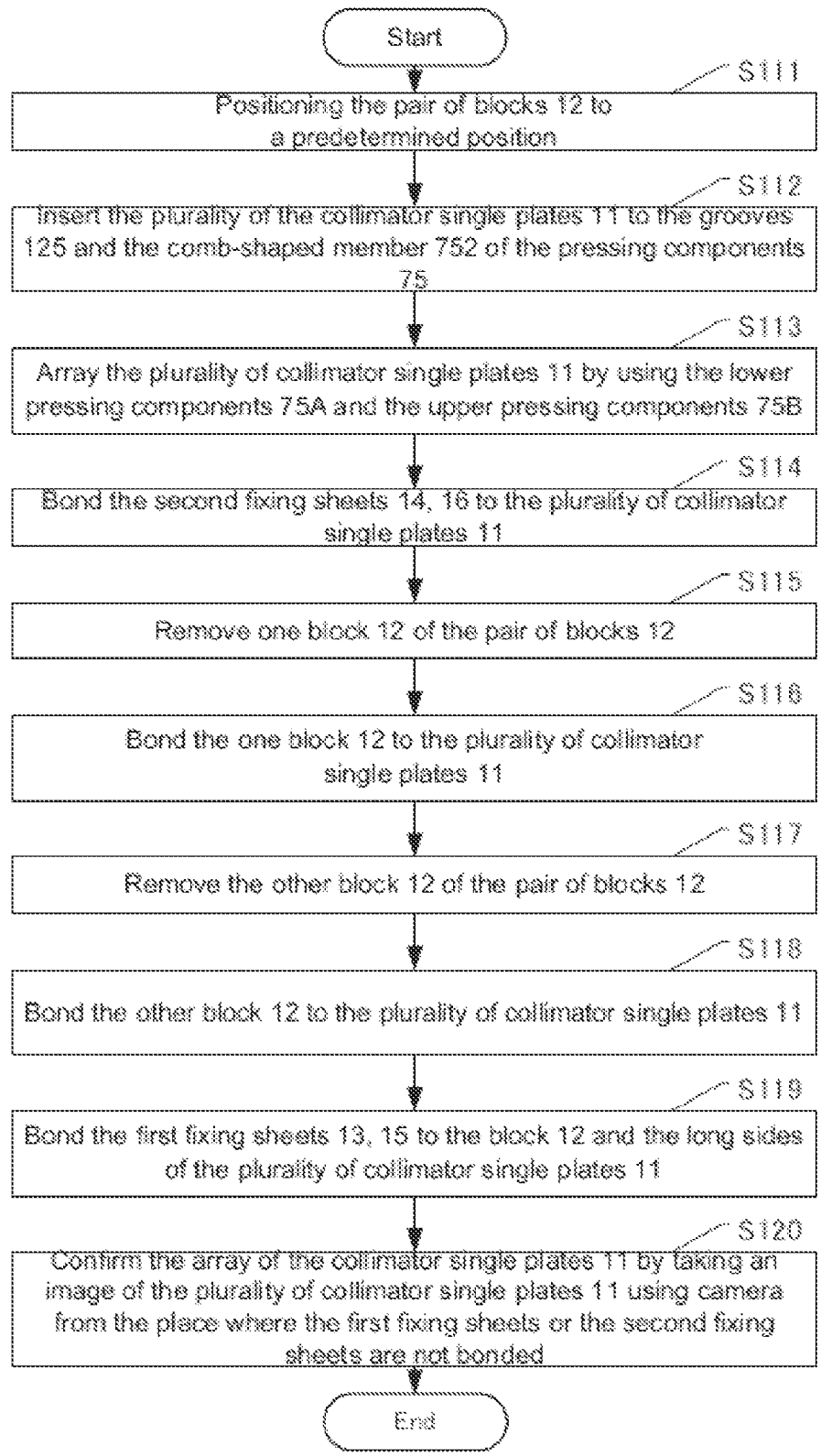
FIG. 16 is a flow chart showing the assembling steps of the second collimator module 10B.

Now, the assembling method of the collimator module 10 will be explained. The assembling steps of the second collimator module 10B in FIG. 8 are explained as an example of the collimator module 10. FIG. 16 is a flow chart showing the assembling steps of the second collimator module 10B.

First of all, the upper jig 70B of the jig 70 (comprising the lower jig 70A and the upper jig 70B) is removed from the jig 70. This enables to assemble a pair of the blocks 12 or the collimator single plate 11 from an upper side. A plurality of cutouts 81 of the comb-shaped member 752 are layered on the cutouts 84 (see FIG. 14 or FIG. 17) of the spring board member 753 of the pressing component 75.

In step S111, a pair of the blocks 12 is fixed to the collimator module fixing block 79 of the lower jig 70A. The pair of blocks 12 is positioned at a predetermined position by the positioning pins or the like.

In step S112, dozens of the collimator single plates 11 are inserted into the first grooves 125 of the blocks 12 and the pressing components 75. More specifically, the long sides 11LS of the dozens of the collimator single plates 11 touch the upper base 88 of the reference board 751 and are inserted into the plurality of cutouts 81 of the comb-shaped member 752 and the cutouts 84 of the spring board member 753. The short sides 11SS of the dozens of the collimator single plates 11 are inserted into the first grooves 125 of the blocks 12.

After the dozens of the collimator single plates 11 are inserted into the cutouts 81 and the cutouts 84, the first incident side fixing sheet 13 and the second incident side fixing sheet 14 are mounted on the long sides 11LS of the collimator single plates 11. In this condition, the long sides 11LS of the collimator single plates 11 are inserted into the second grooves 135, 155, but not yet bonded by an adhesive. Then, the upper jig 70B is attached to the top of the lower jig 70A by the connecting pillars 74.

Figure 17:
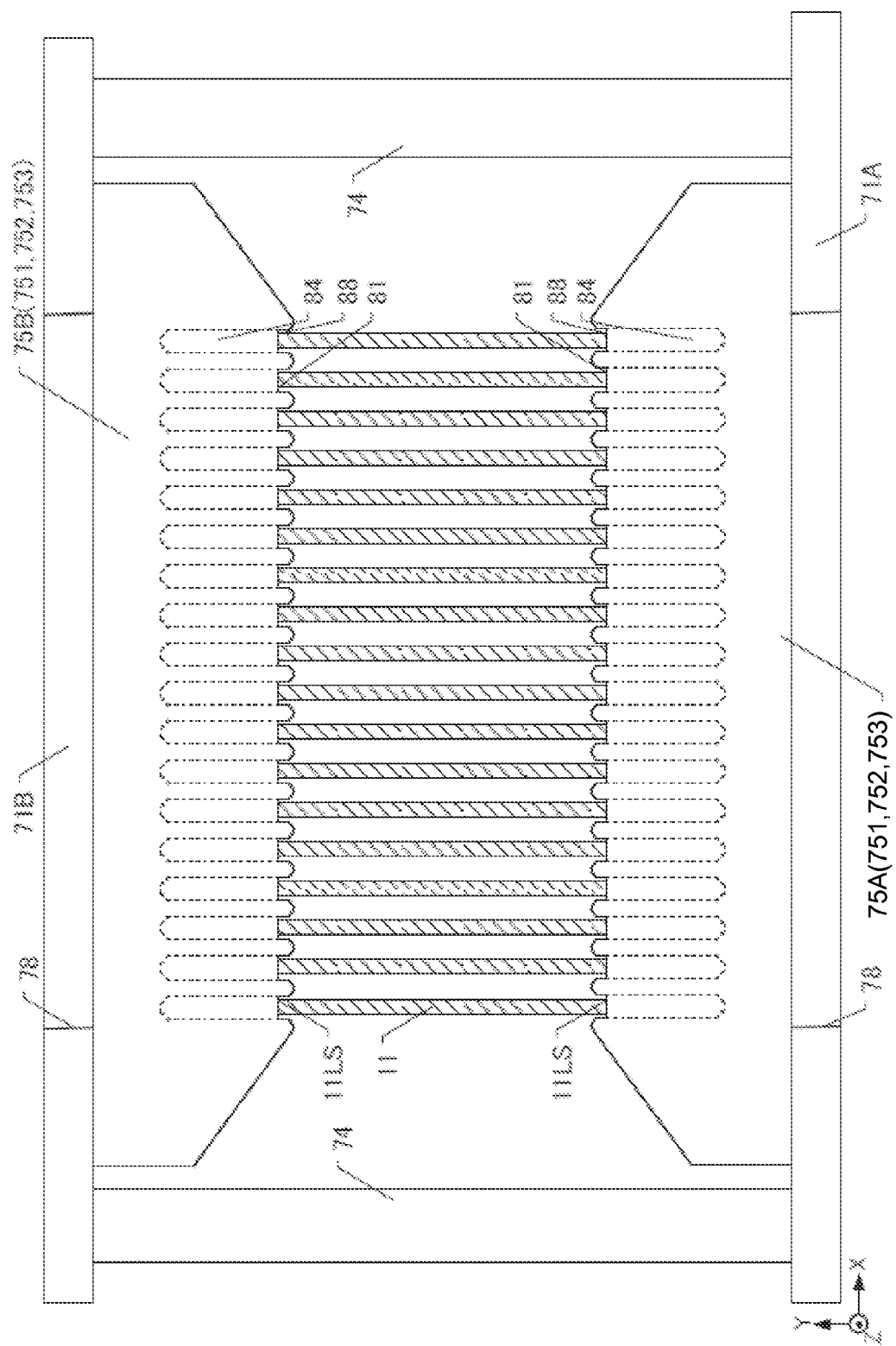
FIG. 17 is a figure that the upper jig 70B is attached to the top of the lower jig 70A.

FIG. 17 is a cross-sectional view along the C-C line of FIG. 12 when the upper jig 70B is attached to the top of the lower jig 70A. Also FIG. 17 shows a condition that dozens of the collimator single plates 11 are inserted to the pressing members 75. As shown in FIG. 17, the plurality of the cutouts 81 of the comb-shaped member 752 and the plurality of the cutouts 84 of the spring board member 753 of the pressing component 75 (see FIG. 14 or FIG. 17) are layered. That is, the cutouts are fully opened (see FIG. 18A).

In step S113, the dozens of the collimator single plates 11 are arrayed by the pressing components 75. The dozens of collimator single plates 11 are arrayed in X-axis direction by using the lower pressing components 75A and the upper pressing components 75B. The spring board member 753 of the lower pressing components 75A and the upper pressing components 75B move in X-axis direction so that the dozens of the collimator single plates 11 are pushed to the side surfaces 125K (see FIG. 5) on −X side of the first grooves 125 of the block 12. The moving condition of the spring board member 753 is explained with FIG. 18B.

Figure 18A:
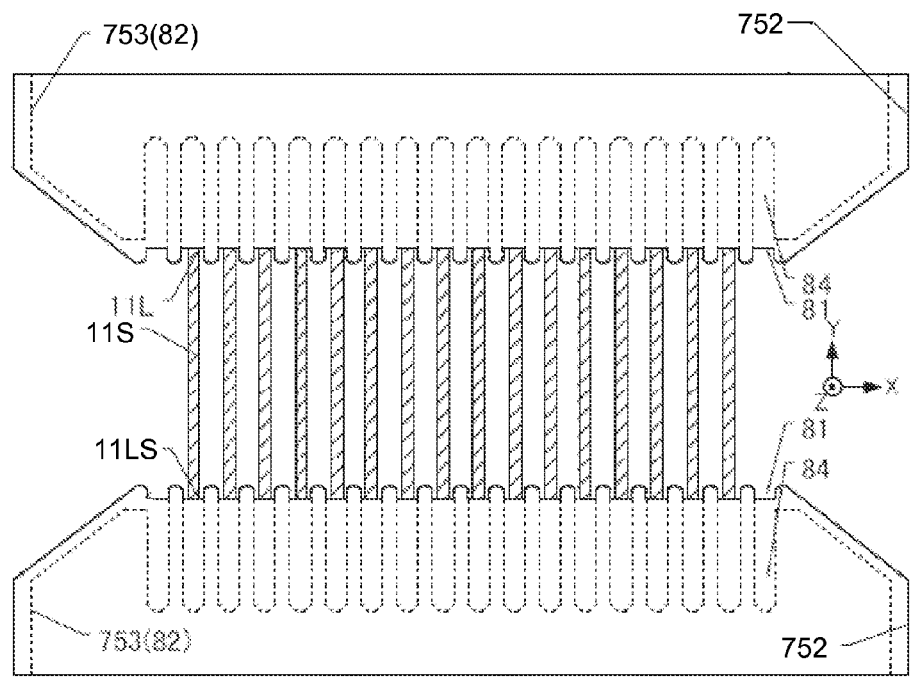
FIG. 18A shows that the pressing component 75 is fully opened.
Figure 18B:
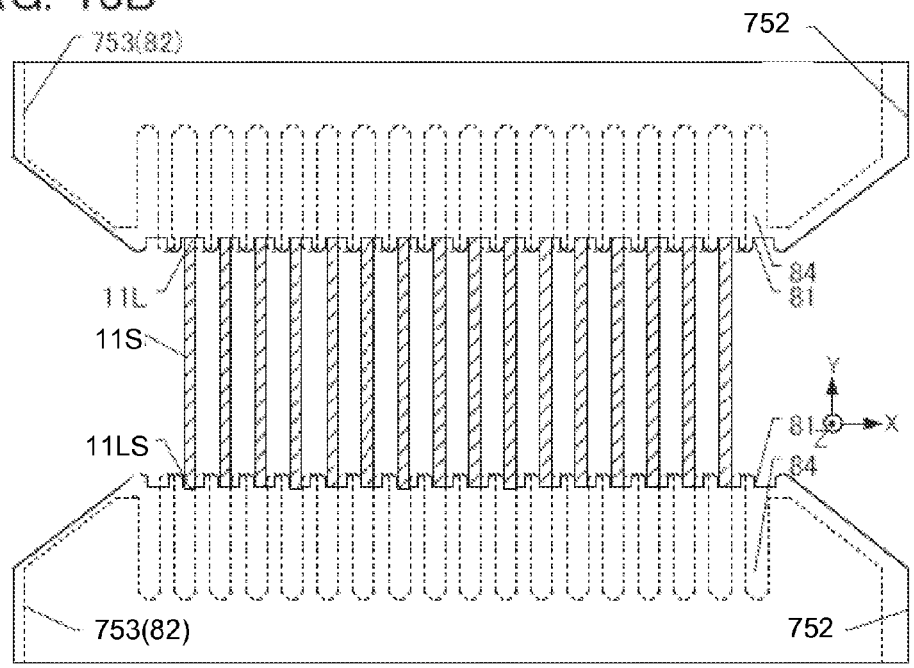
FIG. 18B shows after the pressing component 75 is moved.

FIGS. 18A and 18B are figures for explaining two conditions of the pressing component 75. FIG. 18A shows that the pressing component 75 is fully opened. FIG. 18B shows after the pressing component 75 is moved. For a better understanding, the reference board 751 and the first backing plate 85 and the second backing plate 86 of the spring board member 753 are not shown.

In FIG. 18A, the pressing component 75 is "fully opened" in that the cutouts 81 of the comb-shaped member 752 and the cutouts 84 of the spring portion 82 are completely layered. Thus, dozens of the long sides 11LS of the collimator single plates 11 are easily inserted into the pressing components 75. In a condition that the long sides 11LS of the collimator single plates 11 are inserted into the cutouts 81 and the cutouts 84, the spring portions 82 of the lower pressing components 75A and the upper pressing components 75B move to −X-axis direction so that the dozens of collimator single plates 11 inserted into the cutouts 81 and 84 are also moved to −X-axis direction at a time. As a result, the dozens of the collimator single plates 11 are pushed to the side surfaces 125K on −X side of the first grooves 125 of the block 12 as shown in FIG. 5.

In step S114 of FIG. 16, the second incident side fixing sheets 14 are bonded to the dozens of the long sides 11LS of the collimator single plates 11. In this process, the second incident side fixing sheets 14 are supported by the supporting block 90 against the collimator single plates 11. Then, the jig 70 is turned upside down. In consequence, the excess adhesive is dropped by gravity and the dropped adhesive is removed by wiping with a cloth. After the adhesive is dried, the first emission side fixing sheets 15 and the second emission side fixing sheets 16 are mounted on the long sides 11LS of the collimator single plates 11. Then, the second emission side fixing sheets 16 are bonded to the dozens of the long sides 11LS of the collimator single plates 11. The jig 70 is again turned back to the original position. The excess adhesive applied on the second fixing sheets on incident side 16 is removed by wiping a cloth.

In step S115, one of the pair of blocks 12 is removed from the collimator single plates 11. When the one of block 12 is removed, it is kept fixed to the pillar mount 72 and the collimator module fixing block 79. This is because the side surface 125K on −X side of the first groove 125 of the block 12 acts as a reference for arraying the collimator single plates 11 and it is required for returning the collimator single plates 11 to the original reference position by the pillar mount 72 when it is inserted again.

In step S116, an adhesive is applied to the first grooves 125 of the removed block 12 and the block 12 is returned to the original position of the short sides 11SS of the collimator single plates 11. Then, the first grooves 125 of the block 12 and the short sides 11SS of the collimator single plates 11 are bonded.

In step S117, the other block 12 is removed from the collimator single plates 11.

In step S118, an adhesive is applied to the first grooves 125 of the other block 12 and then it is returned to the short sides 11SS of the collimator single plates 11. Then, the first grooves 125 of the other block 12 and the short sides 11SS of the collimator single plates 11 are bonded.

In step S119, the first incident side fixing sheet 13 and the first emission side fixing sheet 15 are bonded to the incident side surface 121 and the emission side surface 12E of the block 12.

In step S120, the second collimator module 10B is removed from the jig 70 and then inspected. That is, it is inspected to find whether the dozens of collimator single plates 11 are arrayed correctly and fixed to the blocks 12. The dozens of collimator single plates 11 of the second collimator module 10B are checked from the spaces L3 between the first incident side fixing sheet 13 and the second incident side fixing sheet 14, or between adjacent second incident side fixing sheets 14. By a general camera with a visible light, the dozens of the collimator single plates 11 are checked to determine whether they are arrayed properly.

The third collimator module 10C, the forth collimator module 10D, and the fifth collimator module 10E can be made by attaching the third incident side fixing sheet 17 and the third emission side fixing sheet 18, or the supporting sheets 21 and 22 after the second collimator module 10B completed by the above-mentioned assembling steps.

Representative embodiments are described above. It will be understood that these embodiments can be modified or changed while not departing from the spirit and scope of them and/or of the appended claims.

What is claimed is:

1. A collimator module for collimating X-rays comprising:
   a plurality of collimator single plates each having a rectangular shape including a pair of long sides having a first length and a pair of short sides having a second length shorter than the first length of the pair of long sides;
   a pair of blocks comprising a plurality of first grooves extending along an irradiation direction of the X-rays, the short sides of the collimator single plates inserted into the plurality of first grooves of the pair of blocks to support the plurality of collimator single plates in a vertical orientation along the irradiation direction of X-rays; and
   a supporting member configured to cover the long sides of the plurality of the collimator single plates from an incident side and an emission side of the X-rays, the supporting member having an X-ray transmission property and comprising an incident side fixing sheet and an emission side fixing sheet that each include a plurality of second grooves, the long sides of the collimator single plates inserted into the plurality of second grooves to support the plurality of collimator single plates,
   wherein the incident side fixing sheet and the emission side fixing sheet cover the plurality of first grooves and at least a portion of each of the long sides of the plurality of collimator single plates adjacent to the first grooves from the incident side and the emission side of the X-rays, and wherein the collimator module is configured to form a collimator when a plurality of collimator modules are arranged in a channel direction.

2. The collimator module according to claim 1, wherein the incident side fixing sheet and the emission side fixing sheet comprise a first incident side fixing sheet and a first emission side fixing sheet that cover the portion of each of the long sides adjacent to the plurality of first grooves from the incident side and the emission side of the X-rays, and wherein the supporting member further comprises a second incident side fixing sheet and a second emission side fixing sheet that each include the plurality of second grooves to which the long sides of the collimator single plates are inserted, the second incident side fixing sheet and the second emission side fixing sheet covering the long sides of the collimator single plates, wherein gaps are defined between the first incident side fixing sheet and the first emission side fixing sheet and between the second incident side fixing sheet and the second emission side fixing sheet.

3. The collimator module according to claim 2, wherein the supporting member comprises a plurality of second incident side fixing sheets spaced apart from one another and a plurality of second emission side fixing sheets spaced apart from one another.

4. The collimator module according to claim 2, wherein the supporting member further comprises a third incident side fixing sheet and a third emission side fixing sheet that each include a plurality of third grooves to which the long sides of the collimator single plates are inserted, the third incident side fixing sheet and the third emission side fixing sheet covering the long sides of the collimator single plates and positioned within the gaps defined between the first incident side fixing sheet and the first emission side fixing sheet and between the second incident side fixing sheet and the second emission side fixing sheet.

5. The collimator module according to claim 2, wherein the supporting member comprises a pair of supporting sheets extended between the pair of blocks and layered on the first incident side fixing sheet and the first emission side fixing sheet, and wherein the pair of supporting sheets are coupled to the plurality of collimator single plates.

6. The collimator module according to claim 1, wherein each fixing sheet comprises a carbon fiber reinforced plastic that is fixed to the collimator single plates and the pair of blocks by an adhesive.

7. An X-ray detector comprising:
a base member extending in a channel direction;
a plurality of collimator modules arranged in the channel direction on the base member, each of the plurality of collimator modules comprising:
a plurality of collimator single plates each having a rectangular shape including a pair of long sides having a first length and a pair of short sides having a second length shorter than the first length of the pair of long sides;
a pair of blocks comprising a plurality of first grooves extending along an irradiation direction of X-rays, the short sides of the collimator single plates inserted into the plurality of first grooves to support the plurality of collimator single plates in a vertical orientation along the irradiation direction of X-rays; and
a supporting member configured to cover the long sides of the plurality of collimator single plates from an incident side and an emission side of the X-rays, the supporting member having an X-ray transmission property and comprising an incident side fixing sheet and an emission side fixing sheet that each comprise a plurality of second groves, the long sides of the collimator single plates inserted into the plurality of second grooves to support the plurality of collimator single plates, the incident side fixing sheet and the emission side fixing sheet covering the plurality of first grooves of the pair of blocks and at least a portion of each of the long sides of the plurality of collimator single plates adjacent to the first grooves from the incident side and the emission side of the X-rays; and
a plurality of X-ray detector elements set on an emission side of the plurality of collimator modules.

8. The X-ray detector according to claim 7, wherein the incident side fixing sheet and the emission side fixing sheet comprise a first incident side fixing sheet and a first emission side fixing sheet that cover the portion of each of the long sides adjacent to the plurality of first grooves from the incident side and the emission side of the X-rays, and wherein the supporting member further comprises a second incident side fixing sheet and a second emission side fixing sheet that each comprise the plurality of second grooves to which the long sides of the collimator single plates are inserted, the second incident side fixing sheet and the second emission side fixing sheet covering the long sides of the collimator single plates, wherein gaps are defined between the first incident side fixing sheet and the first emission side fixing sheet and between the second incident side fixing sheet and the second emission side fixing sheet.

9. The X-ray detector according to claim 8, wherein the supporting member comprises a plurality of second incident side fixing sheets spaced apart from one another and a plurality of second emission side fixing sheets spaced apart from one another.

10. The X-ray detector according to claim 8, wherein the supporting member further comprises a third incident side fixing sheet and a third emission side fixing sheet that each include a plurality of third grooves to which the long sides of the collimator single plates are inserted, the third incident side fixing sheet and the third emission side fixing sheet covering the long sides of the collimator single plates and positioned within the gaps defined between the first incident side fixing sheet and the first emission side fixing sheet and between the second incident side fixing sheet and the second emission side fixing sheet.

11. An X-ray computed tomography (CT) device for reconstructing a CT image, the X-ray CT device comprising:
an X-ray detector including a base member extending in a channel direction;
a plurality of collimator modules arranged in the channel direction on the base member, each of the plurality of collimator modules comprising:
a plurality of collimator single plates each having a rectangular shape including a pair of long sides having a first length and a pair of short sides having a second length shorter than the first length of the pair of long sides;
a pair of blocks comprising a plurality of first grooves extending along an irradiation direction of the X-rays, the short sides of the collimator single plates inserted into the plurality of first grooves of the pair of blocks to support the plurality of collimator single plates in a vertical orientation along the irradiation direction of X-rays; and a supporting member configured to cover the long sides of the plurality of the collimator single plates from an incident side and an emission side of the X-rays, the supporting member having an X-ray transmission property and comprising an incident side fixing sheet and an emission side fixing sheet that each include a plurality of second grooves, the long sides of the collimator single plates inserted into the plurality of second grooves to support the plurality of collimator single plates, wherein the incident side fixing sheet and the emission side fixing sheet cover the plurality of first grooves and at least a portion of each of the long sides of the plurality of collimator single plates adjacent to the first grooves from the incident side and the emission side of the X-rays; and a plurality of X-ray detector elements set on an emission side of the plurality of collimator modules.

12. The X-ray CT device according to claim 11, wherein the incident side fixing sheet and the emission side fixing sheet comprise a first incident side fixing sheet and a first emission side fixing sheet that cover the portion of each of the long sides adjacent to the plurality of first grooves from the incident side and the emission side of the X-rays, and wherein the supporting member further comprises a second incident side fixing sheet and a second emission side fixing sheet that each include the plurality of second grooves to which the long sides of the collimator single plates are inserted, the second incident side fixing sheet and the second emission side fixing sheet covering the long sides of the collimator single plates, wherein gaps are defined between the first incident side fixing sheet and the first emission side fixing sheet and between the second incident side fixing sheet and the second emission side fixing sheet.

13. The X-ray CT device according to claim 12, wherein the supporting member comprises a plurality of second incident side fixing sheets spaced apart from one another and a plurality of second emission side fixing sheets spaced apart from one another.

14. The X-ray CT device according to claim 13, wherein the supporting member further comprises a third incident side fixing sheet and a third emission side fixing sheet that each include a plurality of third grooves to which the long sides of the collimator single plates are inserted, the third incident side fixing sheet and the third emission side fixing sheet covering the long sides of the collimator single plates and positioned within at least one of the gaps defined between the first incident side fixing sheet and the first emission side fixing sheet and between the second incident side fixing sheet and the second emission side fixing sheet, and gaps defined between adjacent second incident side fixing sheets and between adjacent second emission side fixing sheets.

15. A method for assembling a collimator module comprising:

a plurality of collimator single plates each having a rectangular shape including a pair of long sides having a first length and a pair of short sides having a second length shorter than the first length of the pair of long sides;

a pair of blocks comprising a plurality of first grooves extending along an irradiation direction of X-rays; and a supporting member configured to cover the long sides of the plurality of the collimator single plates from an incident side and an emission side of the X-rays and having an X-ray transmission property, wherein the supporting member comprises:

a first incident side fixing sheet and a first emission side fixing sheet each having a plurality of second grooves and configured to cover the plurality of first grooves of the pair of blocks and at least a portion of each of the long sides of the plurality of collimator single plates adjacent to the first grooves from the incident side and the emission side of the X-rays; and a second incident side fixing sheet and a second emission side fixing sheet that each include the plurality of second grooves, wherein gaps are defined between the first incident side fixing sheet and the first emission side fixing sheet and between the second incident side fixing sheet and the second emission side fixing sheet, the method comprising:

inserting the short sides of the collimator single plates into the plurality of first grooves of the pair of blocks;

arraying the collimator single plates by positioning the collimator single plates against one sidewall surface of each of the first grooves in the channel direction using a pressing component positioned to sandwich the long sides of each of the plurality of collimator single plates;

fixing the long sides of the collimator single plates to the second grooves of the first incident side fixing sheet, the first emission side fixing sheet, the second incident side fixing sheet, and the second emission side fixing sheet, wherein the pressing component is positioned in the gaps defined between the first incident side fixing sheet and the first emission side fixing sheet and between the second incident side fixing sheet and the second emission side fixing sheet; and removing the pressing component from the collimator single plates, wherein the collimator module is configured to form a collimator when a plurality of collimator modules are arranged in a channel direction.

16. The method for assembling a collimator module according to claim 15, wherein the supporting member comprises a plurality of second incident side fixing sheets spaced apart from one another and a plurality of second emission side fixing sheets spaced apart from one another, and wherein fixing the long sides to the second grooves further comprises fixing the long sides of the collimator single plates to the plurality of second incident side fixing sheets and to the plurality of second emission side fixing sheets, wherein the pressing component is positioned in gaps defined between adjacent second incident side fixing sheets and between adjacent second emission side fixing sheets.

17. The method for assembling a collimator module according to claim 15, further comprising inspecting an arrayed state of the plurality of collimator single plates from the gaps after the pressing component is removed from the gaps.

18. The method for assembling a collimator module according to claim 15, wherein the pressing component includes a reference board configured to contact the long sides of the collimator single plates, a comb-shaped portion configured to receive the long sides of the collimator single plates, and a spring board configured to move the long sides of the collimator single plate, and arraying the collimator single plates comprises pushing the collimator single plates against one sidewall surface of each of the first grooves in the channel direction by touching the long sides of the collimator single plates to the reference board and moving the spring board toward the comb-shaped portion.

19. The method for assembling a collimator module according to claim 15, wherein arraying the collimator single plates further comprises pushing a pair of long sides of the collimator single plates using a plurality of pressing components to array the collimator single plates.

20. The collimator module according to claim 3, wherein the supporting member further comprises a third incident side fixing sheet and a third emission side fixing sheet that each include a plurality of third grooves to which the long sides of the collimator single plates are inserted, the third incident side fixing sheet and the third emission side fixing sheet covering the long sides of the collimator single plates and positioned within the gaps defined between adjacent second incident side fixing sheets and between adjacent second emission side fixing sheets.

* * * * *